US009476056B2

United States Patent
Jan et al.

(10) Patent No.: US 9,476,056 B2
(45) Date of Patent: Oct. 25, 2016

(54) RECOMBINANT VECTOR FOR PRODUCING AND SECRETING PEPTIDE OR PROTEIN OF INTEREST BY PROPIONIBACTERIA AND APPLICATIONS THEREOF

(71) Applicants: INSTITUT NATIONAL DE LA SANTE ET DE LA RECHERCHE MEDICALE (INSERM), Paris (FR); INSTITUT NATIONAL DE LA RECHERCHE AGRONOMIQUE, Paris (FR)

(72) Inventors: Gwenael Jan, Rennes (FR); Marie-Thérèse Dimanche-Boitrel, Melesse (FR); Hélène Falentin, Mordelles (FR); Charles Halouze, Rennes (FR)

(73) Assignees: UNIVERSITE DE RENNES 1, Rennes (FR); INSTITUT NATIONAL DE LA SANTE ET DE LA RECHERCHE MEDICALE (INSERM), Paris (FR); INSTITUT NATIONAL DE LA RECHERCHE AGRONOMIQUE, Paris (FR)

( * ) Notice: Subject to any disclaimer, the term of this patent is extended or adjusted under 35 U.S.C. 154(b) by 24 days.

(21) Appl. No.: 13/679,344

(22) Filed: Nov. 16, 2012

(65) Prior Publication Data
US 2014/0154213 A1    Jun. 5, 2014

Related U.S. Application Data

(63) Continuation-in-part of application No. 13/698,213, filed as application No. PCT/EP2011/057718 on May 12, 2011, now abandoned.

(60) Provisional application No. 61/333,974, filed on May 12, 2010.

(30) Foreign Application Priority Data

May 12, 2010    (FR) ..................................... 10 53750

(51) Int. Cl.
*C12N 15/74* (2006.01)
*C07K 14/705* (2006.01)

(52) U.S. Cl.
CPC ......... *C12N 15/74* (2013.01); *C07K 14/70578* (2013.01); *C07K 2319/02* (2013.01); *Y02P 20/582* (2015.11)

(58) Field of Classification Search
None
See application file for complete search history.

(56) References Cited

FOREIGN PATENT DOCUMENTS

| WO | WO 96/11277 A1 | 4/1996 |
| WO | WO 03/045405 A2 | 6/2003 |
| WO | WO 03/061226 A1 | 7/2003 |
| WO | WO 03/063593 A1 | 8/2003 |
| WO | WO 2008/104890 A2 | 9/2008 |
| WO | WO 2009/111177 A2 | 9/2009 |

OTHER PUBLICATIONS

Dilks, et al. (2003) "Prokaryotic Utilization of the Twin-Arginine Translocation Pathway: a Genomic Survey", Journal of Bacteriology, 185(4): 1478-83.*
http://en.wikipedia.org/wiki/S-layer, no authors listed, published by Wikipedia, San Francisco, CA, no journal, volume, issue or page numbers, 2 pages long.*
Hynonen, et al. (2013) "Lactobacillus surface layer proteins: structure, function, and applications", Applied Microbiology and Biotechnology, 97(12): 5225-43.*
Brede, et al., Heterologous Production of Antimicrobial Peptides in Propionibacterium Freudenreichii, Applied and Environmental Microbiology, Dec. 2005, pp. 8077-8084, vol. 71, No. 12, XP-002612902.
Choo et al., A Comprehensive Assessment of N-Terminal Signal Peptides Prediction Methods. BMC Bioinformatics, Dec. 3, 2009, vol. 10 (Suppl 15), pp. 112.
Dherbécourt, et al., Identification of a Secreted Lipolytic Esterase in Propionibacterium Freudenreichii, a Ripening Process Bacterium Involved in Emmental Cheese Lipolysis, Applied and Environmental Microbiology, Feb. 2010, pp. 1181-1188, vol. 76, No. 4, XP-002612901.
Lan et al., Increased Induction of Apoptosis by Propionibacterium Freudenreichii TL133 is Colonic Mucosal Crypts of Human Microbiota-Associated Rats Treated with 1,2-dimethylhydrazine, British Journal of Nutrition, 2008, pp. 1251-1259, XP-002612903.

* cited by examiner

*Primary Examiner* — Robert M Kelly
(74) *Attorney, Agent, or Firm* — Birch, Stewart, Kolasch & Birch, LLP

(57) ABSTRACT

The present invention relates to a recombinant vector for expressing and secreting, by a *Propionibacterium*, at least one eukaryotic peptide or protein of interest, comprising at least: under the control of at least one suitable promoter, at least one nucleic acid sequence encoding a propionibacterial signal peptide and, at least one nucleic acid sequence encoding said eukaryotic peptide or protein of interest; wherein said at least one nucleic acid sequence encoding a propionibacterial signal peptide is translationally fused to said at least one nucleic acid sequence encoding said eukaryotic peptide or protein of interest. The invention further relates to the uses of such a vector in the pharmaceutical field or for the large-scale production of peptides or proteins of interest.

14 Claims, 6 Drawing Sheets

Figure 2:
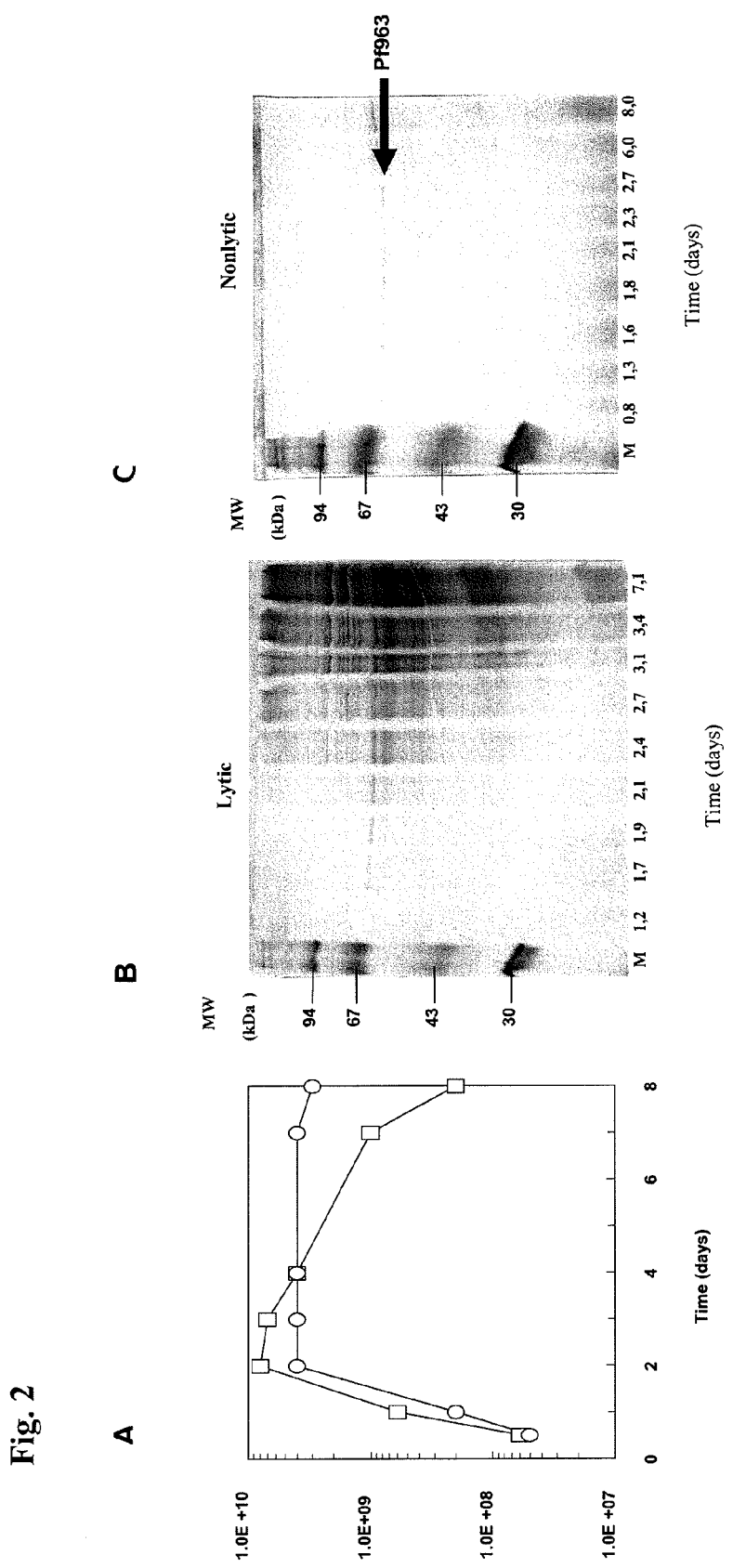

Fig. 1
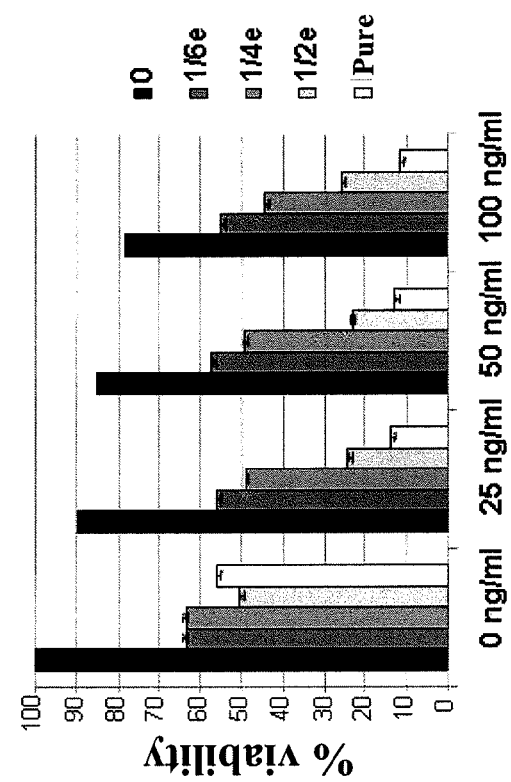
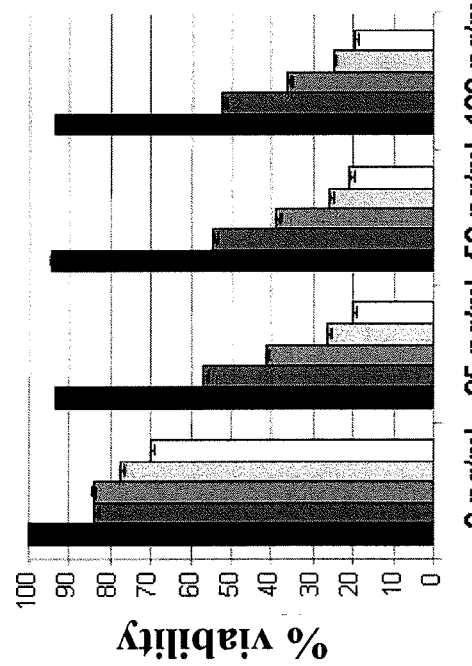

Fig. 5

```
DNA: GTGAATCCCTTCGTCAAGACGGCGCGCGTGGCTATCACCTCGACGCTGGTG
 +1:  M  N  P  F  V  K  T  A  R  V  A  I  T  S  T  L  V

DNA: GCAGGCTCGCTGGCCACTGCCAGCCTCGTGTTTGCACCACTTGCACAGGCC
 +1:  A  G  S  L  A  T  A  S  L  V  F  A  P  L  A  Q  A

DNA: GAAAGCTTAGTGAGAGAAAGAGGTCCTCAGAGAGTAGCAGCTCACATAACT
 +1:  E  S  L  V  R  E  R  G  P  Q  R  V  A  A  H  I  T

DNA: GGGACCAGAGGAAGAAGCAACACATTGTCTTCTCCAAACTCCAAGAATGAA
 +1:  G  T  R  G  R  S  N  T  L  S  S  P  N  S  K  N  E

DNA: AAGGCTCTGGGCCGCAAAATAAACTCCTGGGAATCATCAAGGAGTGGGCAT
 +1:  K  A  L  G  R  K  I  N  S  W  E  S  S  R  S  G  H

DNA: TCATTCCTGAGCAACTTGCACTTGAGGAATGGTGAACTGGTCATCCATGAA
 +1:  S  F  L  S  N  L  H  L  R  N  G  E  L  V  I  H  E

DNA: AAAGGGTTTTACTACATCTATTCCCAAACATACTTTCGATTTCAGGAGGAA
 +1:  K  G  F  Y  Y  I  Y  S  Q  T  Y  F  R  F  Q  E  E

DNA: ATAAAAGAAAACACAAAGAACGACAAACAAATGGTCCAATATATTTACAAA
 +1:  I  K  E  N  T  K  N  D  K  Q  M  V  Q  Y  I  Y  K

DNA: TACACAAGTTATCCTGACCCTATATTGTTGATGAAAAGTGCTAGAAATAGT
 +1:  Y  T  S  Y  P  D  P  I  L  L  M  K  S  A  R  N  S

DNA: TGTTGGTCTAAAGATGCAGAATATGGACTCTATTCCATCTATCAAGGGGGA
 +1:  C  W  S  K  D  A  E  Y  G  L  Y  S  I  Y  Q  G  G

DNA: ATATTTGAGCTTAAGGAAAATGACAGAATTTTTGTTTCTGTAACAAATGAG
 +1:  I  F  E  L  K  E  N  D  R  I  F  V  S  V  T  N  E

DNA: CACTTGATAGACATGGACCATGAAGCCAGTTTTTTCGGGGCCTTTTTAGTT
 +1:  H  L  I  D  M  D  H  E  A  S  F  F  G  A  F  L  V

DNA: GGCTAACTGCA    (SEQ. ID NO: 42)
 +1:  G  *  L      (SEQ. ID NO: 43)
```

RECOMBINANT VECTOR FOR PRODUCING AND SECRETING PEPTIDE OR PROTEIN OF INTEREST BY PROPIONIBACTERIA AND APPLICATIONS THEREOF

CROSS REFERENCE TO RELATED APPLICATIONS

This application is a Continuation-In-Part of application Ser. No. 13/698,213 filed on Nov. 15, 2012, abandoned, which is a U.S. national phase of PCT International Application No. PCT/EP2011/057718 filed on May 12, 2011, which claims the benefit of U.S. Provisional Application No. 61/333,974 filed on May 12, 2010 and to Patent Application No. 1053750 filed in FRANCE, on May 12, 2010. The entire contents of all of the above applications is hereby incorporated by reference.

The present invention relates to the field of genetic engineering applicable in particular in the pharmaceuticals, chemicals, agri-foods and cosmetics industries, etc.

More precisely, the present invention relates to a recombinant vector for expressing and secreting, by a *propionibacterium*, one or more amino acid sequences of interest, wherein said vector comprises at least:
  under the control of at least one suitable promoter,
  at least one nucleotide sequence coding for a propionibacteria signal peptide and, in translational fusion with said nucleotide sequence,
  one or more nucleotide sequences coding for said amino acid sequence or sequences of interest.

In other words, the invention relates to a recombinant vector, particularly for expressing and secreting, by a *propionibacterium*, at least one eukaryotic peptide or protein of interest, comprising at least:
  under the control of at least one suitable promoter,
  at least one nucleic acid sequence encoding a propionibacterial signal peptide and,
  at least one nucleic acid sequence encoding said eukaryotic peptide or protein of interest;
wherein said at least one nucleic acid sequence encoding a propionibacterial signal peptide is translationally fused to said at least one nucleic acid sequence encoding said peptide or protein of interest.

The invention also relates to the uses of such a vector in the pharmaceutical field or for the large-scale production of peptides or proteins whose activity is of interest in industries as diverse as pharmaceuticals, chemicals, agri-foods, cosmetics, etc.

There are today a large number of methods and means for the large-scale production of peptides and/or proteins. With traditional chemical synthesis, which is hardly suitable for large-scale production of proteins comprising several dozen amino acids, the generally preferred method is synthesis in vivo, that is, in living biological systems. Many commercial enterprises in France and elsewhere have made a principal business of said production, and thus propose technologies based on genetic engineering and biotechnology to provide industrial quantities of peptides and/or proteins, preferably active and purified. Depending on needs, it is now possible to have recourse to various living systems such as bacteria (e.g., *Escherichia coli*), yeasts (e.g., *Saccharomyces cerevisiae, Pichia pastoris*), insect cells (baculovirus, Sf9, Sf21, etc.), plant cells and mammalian cells (e.g., CHO, HEK, COS, etc.).

Nevertheless, there still does not exist, at present, a "perfect" living system, that is to say, a system that has universal application (in particular to express any protein and to produce any quantity) and is at the same time simple to make use of, powerful, reliable and affordable.

The present invention aims precisely at mitigating these shortcomings while proposing for the first time the use of propionibacteria as living systems for producing and secreting recombinant peptides and proteins, especially from eukaryotic origin.

Propionibacteria (PB) and, more particularly, dairy propionibacteria (DPB) (notably *Propionibacterium freudenreichii*) have a particular metabolism which rests on the anaerobic conversion of sugars or lactic acid into short-chain fatty acids (SCFA), such as propionate, acetate and valerate SCFA. These bacteria are used principally as ripening starter for cooked, pressed cheeses. Until now, few scientific teams or research and development laboratories have been interested in these bacteria. Several probiotic applications are known for said bacteria (for example, the Propiofidus® formulation marketed by Laboratoires Standa, France). They are indeed able to modulate the complex ecosystem of the colon in terms of microbial flora (Bougle et al., 1999) and enzymatic activities (Zarate et al., 2000).

The Inventors have recently cloned and sequenced the genome of the probiotic anaerobic firmicute bacterium *Propionibacterium freudenreichii* (Falentin et al., 2010, Plos One; Genbank accession No. FN806773). This bacterium has in particular cytotoxic properties with respect to colon cancer cells (Jan et al., 2002; Lan et al., 2007). Among other notable properties, it adheres to colonic epithelial cells and has no toxic effect on healthy cells (Lan et al., 2008).

Although they grow rather slowly, propionibacteria have the considerable advantage of being naturally able to secrete peptides and proteins into the extracellular medium, thus facilitating the recovery of said peptides and proteins without denaturation and without deterioration of the producing cells which can thus be advantageously recycled. These bacteria are very robust and adapt to particular media (such as media containing milk or milk derivatives, e.g., whey, and media containing molasses) that are possibly hostile to the growth and development of other living systems (presence in the medium of lactic acid, salt, etc.), and have good tolerance with respect to variations, changes or disturbances of the environmental conditions likely to occur during large-scale culture operations. Moreover, they can be described as "natural antifungals" because they naturally produce metabolites (for example, propionate) that inhibit the development of contaminating fungi. Furthermore, they are able to produce recombinant proteins of significant size (for example, proteins of more than 500 amino acids) and can even produce several different proteins simultaneously (for example, more than a dozen different proteins).

Propionibacteria are thus completely suitable to serve as living "factories" for the large-scale production of recombinant peptides and proteins of interest, in particular in the context of in vitro or ex vivo processes or applications.

But their utility does not stop there. Indeed, in mammals, including humans, propionibacteria are naturally able to target the intestine where their survival time can reach roughly two weeks, compared to that of lactic bacteria in particular which, although they are natural hosts of this ecosystem, is only two or three days on average. Thus, propionibacteria can also be used as tool for specific addressing or targeting in vivo for colon delivery of peptides and/or proteins of interest, in particular of therapeutic interest.

Some major advantages of propionibacteria over various other bacteria proposed so far for use in anti-tumoral therapy (e.g., in WO 01/25397 in the name of Vion Pharmaceuticals, Inc. and in WO 2009/111177 in the name of Mount Sinai School of Medicine of New York University) are that propionibacteria per se are an efficient and specific antitumoral agent that can safely be used in mammals, in particular in humans. This inherent property of propionibacteria can thus be further enhanced upon using propionibacteria to deliver therapeutic agents, such as drugs, to eradicate tumor cells while at the same time preventing damage to normal cells. To do so, propionibacteria do not need to be genetically attenuated or enhanced by genomic mutations as it is the case for other bacteria such as *Clostridium, Salmonella, Listeria*, and the like. propionibacteria eventually are a "super" anti-tumoral agent thanks to both their intrinsic anti-tumoral properties and their ability to efficiently, specifically and safely deliver other anti-tumoral drugs in order to kill cancer cells.

Thus, the present invention relates to a recombinant vector for expressing and secreting, by propionibacteria, one or more eukaryotic amino acid sequences of interest, comprising at least:
  under the control of at least one suitable promoter,
  at least one nucleotide sequence coding for a propionibacteria signal peptide and, in translational fusion with said nucleotide sequence,
  one or more nucleotide sequences coding for said eukaryotic amino acid sequence or sequences of interest.

In other words, the invention relates to a recombinant vector, particularly for expressing and secreting, by a *propionibacterium*, at least one eukaryotic peptide or protein of interest, comprising at least:
  under the control of at least one suitable promoter,
  at least one nucleic acid sequence encoding a propionibacterial signal peptide and,
  at least one nucleic acid sequence encoding said eukaryotic peptide or protein of interest;
wherein said at least one nucleic acid sequence encoding a propionibacterial signal peptide is translationally fused to said at least one nucleic acid sequence encoding said peptide or protein of interest.

Unless defined otherwise, all technical and scientific terms used herein have the same meaning as commonly understood to one skilled in the relevant art.

For convenience, the meaning of certain terms and phrases employed in the specification, examples and claims are provided.

A vector can be a cloning or an expression vector. The vectors according to the invention can be viral vectors such as bacteriophages, or non-viral, such as plasmid vectors. A plasmid vector is a non-viral DNA molecule hosted by a cell, distinct from the natural chromosomal DNA of said host cell and capable of autonomous replication. The choice of plasmid vector and, more particularly, the origin of replication it carries thus depend on the host cell. According to the type of host cell, several copies of a plasmid vector and/or several different plasmid vectors can be hosted simultaneously. A plasmid vector according to the invention can possibly be carried by (or "integrated in" or "inserted in") the chromosome of the host cell.

A "recombinant vector" is a vector obtained by traditional molecular biology and genetic engineering techniques, in which one or more exogenous nucleotide sequences have been inserted (or cloned).

The recombinant vector according to the present invention, for expressing and secreting, by a *propionibacterium*, at least one eukaryotic peptide or protein of interest allows the expression and secretion of said peptide or protein by a *propionibacterium*. Indeed, it carries a nucleotide sequence which is transcribed and then translated in the host cell, to produce the peptide or protein of interest. It is thus an "expression" or "production" or "synthesis" vector for said peptide or protein of interest.

The peptide or protein of interest expressed via said recombinant vector according to the invention is transported towards the outside of the host cell. The terms "secretion," "transport towards the outside of the host cell," "export" and "externalization" are equivalent herein and mean that the peptide or protein of interest is expressed and then is exposed to the extracellular medium. Subject to this exposure, it can possibly remain anchored to the membrane of the host cell. However, preferably, the peptide or protein of interest expressed by the host cell is "released" (or "delivered" or "sorted out") into the extracellular medium.

The "extracellular medium" is the medium surrounding the host cell, in particular a *propionibacterium*. It is understood herein that the expressions "extracellular medium," "exterior medium," "external medium," "surrounding medium" and "environment" are synonymous. In some embodiments of the present invention, the *propionibacterium* is grown in vitro or ex vivo (use of the *propionibacterium* as a "factory" to produce the peptide and/or protein of interest). In this case, the extracellular medium is the culture medium. It can also be the supernatant of the culture after separation of the biomass (for example, after cell pellets are centrifuged and separated). In other embodiments, the *propionibacterium* hosting the recombinant vector is administered to a mammal, in particular a human, for in situ expression and delivery of the peptide and/or protein of interest (use of the *propionibacterium* hosting said vector as a specific targeting tool for colon delivery of said peptide and/or protein of interest). In this case, the extracellular medium is the ecosystem of the mammal, more particularly its intestine, and even more particularly its colon.

In the context of the present invention, an "amino acid sequence" is a sequence of a peptide or a protein, as well the one of fragments, analogs, derivatives and combinations of peptides and proteins.

A protein or peptide "fragment" is a smaller peptide or protein, having an amino acid sequence included in the one of the initial peptide or protein. A protein "fragment" could be a peptide, for example.

"Analog" refers to any modified version of an initial compound, in this case a protein or a peptide, wherein said modified version is natural or synthetic, and wherein one or more atoms, such as carbon, hydrogen or oxygen atoms, or heteroatoms such as nitrogen, sulfur or halogen, have been added or removed from the structure of the initial compound, so as to obtain a new molecular compound.

A "derivative" in the context of the invention is any compound that has a resemblance or a structural motif in common with a reference compound (in this case a protein or a peptide). This definition further includes, on the one hand, compounds that, alone or with other compounds, can be precursors or intermediate products in the synthesis of a reference compound, via one or more chemical reactions, and, on the other hand, compounds that can be formed from said reference compound, alone or with other compounds, via one or more chemical reactions. Thus, the term "derivative" covers at least protein and/or peptide hydrolysates, in particular tryptic hydrolysates, hydrolysate fractions and mixtures of hydrolysates and/or hydrolysate fractions. This definition also covers peptidomimetics or pseudopeptides, which are small molecules that mimic the bioactive properties of a reference peptide (Patch et al., 2002).

Moreover, the terms "analog" and "derivative" of a peptide or protein cover, for example, a peptide or a protein that is glycosylated or phosphorylated or has undergone any grafting of a chemical group.

The terms "nucleotide sequence" or a "nucleic acid sequence" according to the invention refer to the sequence of a nucleic acid molecule, DNA and RNA, wherein the former can be genomic DNA, plasmid DNA, recombinant DNA or complementary DNA (cDNA), for example, and the latter can be messenger RNA (mRNA), ribosomal RNA (rRNA) or transfer RNA (tRNA). Preferably, the nucleotide or nucleic acid sequences of the invention are sequences of a DNA molecule.

For the sake of convenience, when the invention refers to "a" vector, "a" protein or "a" nucleotide or amino acid sequence, etc., it is understood that "a" or "the" also covers the use of several vectors, proteins, sequences, etc.

The recombinant vector for expressing and secreting, by a *propionibacterium*, at least one eukaryotic peptide or protein of interest according to the present invention comprises at least one suitable promoter for the expression of said peptide and/or protein of interest in a *propionibacterium*. Particularly, said suitable promoter is a promoter for bacterial RNA polymerase, in particular for propionibacterial RNA polymerase. Said suitable promoter can be a constitutive and/or inducible promoter well known by one skilled in the art. Preferably, said promoter is inducible. The promoter can be developmentally regulated, inducible or tissue specific, preferably inducible in the digestive tract. Preferably, said promoter is a promoter of propionic origin, in particular of *P. freudenreichii* origin, such as the promoter of protein PF963 of *P. freudenreichii*, used by the Inventors in the examples below. More preferably, said promoter is a strong propionic promoter. As noted by the Inventors, it could be advantageous to use a promoter ensuring "basic" constitutive expression which could be strengthened by induced expression under particular conditions (for example, conditions of digestive stress). In one embodiment, said suitable promoter is the promoter of a gene encoding a surface layer protein of a *Propionibacterium freudenreichii*.

Unexpectedly, the Inventors have shown that said promoters of genes encoding a surface layer protein of a *Propionibacterium freudenreichii* in combination with signal peptides of genes encoding a surface layer protein of a *Propionibacterium freudenreichii* allow the secretion into the extracellular medium of a peptide and/or a protein of interest by a *propionibacterium* at a level up to 100 times greater than that obtained with other promoters and peptide signals.

These surface layer proteins have notably been described in the article of Lortal et al. (1993).

In particular, said suitable promoter is the promoter of a gene encoding a surface layer protein of a *Propionibacterium freudenreichii*, said surface layer protein being selected from the group consisting of the surface layer protein A, the surface layer protein B, the surface layer protein C, the surface layer protein D, the surface layer protein E and the surface layer protein F, in particular of the surface layer protein A.

In particular, said suitable promoter is the promoter of the gene encoding the surface layer protein A of *P. freudenreichii* CIRM BIA 118 strain.

The sequences of suitable promoters according to the present invention can also be the sequences having at least 80%, more particularly at least 85%, at least 86%, at least 87%, at least 88%, at least 89%, at least 90%, at least 91%, at least 92%, at least 93%, at least 94%, at least 95%, at least 96%, at least 97%, at least 98% and even more particularly at least 99% of identity with the sequence of the promoter of a gene encoding a surface layer protein of a *Propionibacterium freudenreichii* over the entire length of said sequence and corresponding to a promoter.

Advantageously, the vector according to the invention will contain at least two suitable promoters such as defined above which, even more advantageously, will be situated preferably in a series (but not necessarily coupled to each other), in order to increase the expression level of the peptide and/or protein of interest ("expression booster" effect).

The recombinant vector according to the present invention comprises at least one nucleotide sequence encoding a propionibacterial signal peptide for the secretion, in particular into the extracellular medium, of a peptide and/or protein of interest. In other words, the recombinant vector of the invention comprises at least one nucleic acid sequence encoding a propionibacterial signal peptide, said sequence being translationally fused to at least one nucleic acid sequence encoding a peptide or protein of interest, allowing the secretion, in particular into the extracellular medium, of said peptide or protein, particularly by a *propionibacterium*. In particular, said propionibacterial signal peptide is a propionibacterial secretion signal peptide, allowing the secretion, in particular into the extracellular medium, of said peptide or protein of interest, particularly by a *propionibacterium*. Preferably, a signal peptide of a *propionibacterium* selected from dairy *propionibacterium* and so-called "cutaneous" *propionibacterium* (CPB) can be used. Among other examples, the following dairy *propionibacterium* can be cited: *Propionibacterium freudenreichii, P. jensenii, P. thoenii P. acidipropionici* and *P. microaerophilum*. The following cutaneous *propionibacterium* can also be cited: *P. acnes, P. granulosum, P. avidum* and *P. propionicum*. Even more preferably, a signal peptide of a *propionibacterium* selected from the following species can be used: *Propionibacterium freudenreichii*, more particularly the subspecies *P. freudenreichii* subsp. *freudenreichii* and *P. freudenreichii* subsp. *shermanii*, and *Propionibacterium acnes*, wherein said *propionibacterium* is preferentially *P. freudenreichii* subsp. *shermanii*. More preferentially, a nucleotide sequence coding for a signal peptide can be selected from the following sequences:

sequences SEQ ID NO: 1 to 18 (see table I below);
complementary sequences of same;
sequences at least 80% similar to same or to complementary sequences of same; and
sequences at least 80% hybridizable in strict conditions with same or with complementary sequences of same.

Table I below presents the nucleotide (NT) sequences mentioned above, as well as the corresponding amino acid (AA) sequences, identified following sequencing by the Inventors of the *P. freudenreichii* genome.

TABLE I

| Protein | | SEQ ID NO | |
|---|---|---|---|
| identified Putative signal peptide | | NT | AA |
| PF# 1058 | MSKTLSRIASVASVAALAGSITVIAGQNASA-DS<br>Atgtcaaagacactctctcggatcgcatccgtcgcttcggttg<br>Ccgcgctcgccggcagcatcaccgtcatcgccgggcagaa<br>cgcgtccgccgacagc | 1 | 19 |
| PF# 1328 | MKNGLKTLLIGGVGIATLAVGGVGTAIA-DN<br>Gtgaagaacggtctcaagaccctgctcattggtggagtcgg<br>Catcgcgaccccttgcggtcggcggcgtcggaactgccatcg<br>cagacaat | 2 | 20 |
| PF# 1347 | MRSTTTKAFAGVAVLALALAGCGSNSGSSTKSA-DS<br>Atgcgatccaccacgacgaaggcgtttgccggtgtcgctgtgctggcgct<br>Ggcgcttgctggctgcggctcgaattcgggctcgtccaccaagtcggccg<br>acagc | 3 | 21 |
| PF# 146 | MLTRKRVVAAGAAATLSLTAFAGLQPASA-AT<br>Atgctcactcgcaagagagtggttgcagcgggagctgccgcc<br>Accctgtccctcacggcgttttgccgggttgcagcccgccagcg<br>ccgccacc | 4 | 22 |
| PF# 1885 | MGFRVGRRPLIGAVLAGSMATLVGCSTSGSGSGA-SS<br>Atgggattcagggttggccgtcgtcccctcatcggggcagttctcgccgggtc<br>Gatggcaacactcgtgggctgttccacctcgggtagcggcagtggagcctc<br>cagc | 5 | 23 |
| PF# 190 | MQALQGRRRSRRVMAAAVAALTAMTVLPSQLNAVA-AP<br>Atgcaggccctccaaggaaggcgccggtcacgacgggtgatggcggccgc<br>Ggtagcagccctcaccgccatgaccgtgctgccctcccagctcaacgccgttg<br>ctgcaccc | 6 | 24 |
| PF# 2074 | MSTGRMKFIKLAVPVIVACCLTPMAALA-DV<br>Atgtccactggccgcatgaagttcatcaagctggcagttcctg<br>tcatcgttgcctgctgcttgacgccaatggctgccttagctgatgtg | 7 | 25 |
| PF# 241 | MAMRARHGVVRLGLVCLTALAVFGTANVSGQVAVMA-EG<br>Atggcgatgagggcacgtcacggcgtcgtccggcttggtctggtctgtctcaccgc<br>attggcggtcttcggcacggcaaatgtgtcgggtcaggttgcggtgatggctgagggc | 8 | 26 |
| PF# 2732 | MNQALSTMRLKIGDSTKRIRIFFVVMAVAITLLA-GR<br>Ttgaaccaggccctgtcgacgatgcgcctgaagatcggcgactccacc<br>Aagcgcatccggatcttcttcgtcgtgatggccgtggcgatcaccctgctc<br>gcgggacgg | 9 | 27 |
| PF# 279 | MRRRTTIAALAAVLSFSPLAAQA-AP<br>Atgcgacgtcgcaccacgattgcagccctcgctg<br>Ctgtcttgagtttcagtcccctggccgcccaggccg<br>caccc | 10 | 28 |
| PF# 2818 | MPSHAVRETRANKLRRFLRPTVAQGVLGIAFCLVAAVGVVQI-RS<br>Atgcctagtcatgcggtgcgggagacgcgggcgaacaagttgcgccggttcctgcggcc<br>c<br>Accgttgcccagggcgtgctcggtatcgcgttctgcctcgtggccgccgtcggcgtggtg<br>ca<br>gatccgctcc | 11 | 29 |
| PF# 2932 | MSRIQLPRLSRIAIAAAASAALIGTSFIAPATAFA-AP<br>Atgtcacggattcaactccccccggctgagccggattgcgatcgcagc<br>Agcagcttccgctgccctgatcggcaccagcttcatcgcccccggcca<br>cggccttttgccgcgccg | 12 | 30 |
| PF# 3042 | MKRRTLLGTLGIMGLSVPLAACS-SK<br>Ctagccgaccttctcggccttgctggccaggtcgtc<br>ggggatcgtgacccccatcagggaggcggccttctcatt | 13 | 31 |
| PF# 3412 | MVTGGNDMPSKRITTWPGISALSALIAGMLLAPLPVAA-DG<br>Ttagttgttggggacgaggagggagtggagttcgatgacgtcgagggtgggtgc<br>Ggtgcggggcgggtgatggtttcggtgccggtgtgtccttgggcggtccaggtg<br>atggtccaggt | 14 | 32 |
| PF# 3427 | MAMVMASLAMFGASRASA-AD<br>Tcagccagttggtgccggccttggcgtcgg<br>cggcgtgggatacacgcggaactgggcgcc | 15 | 33 |

TABLE I-continued

| Protein identified | Putative signal peptide | SEQ ID NO NT | AA |
|---|---|---|---|
| PF# 527 | MFISRFRRAAAVGLAAVTALSATACSGSSSSSSSA-SS<br>Atgttcatttcgcgcttccgtcgtgcggctgcggtcggcctggccgc<br>Cgtcaccgcattgtccgccactgcctgtagcggttcctcgtcgtcgtc<br>cagctcatccgcgagctcg | 16 | 34 |
| PF# 876 | MKSATRRPLTRWIVAFGVVLVLVIAGSVGLHASG-AL<br>Atgaagtccgcgacgcgacgcccgctgacgcgctggattgtcgccttcg<br>Gggtggtgttggtgctggtcatcgccgggtcggtggggctgcatgcctccg<br>gtgccctg | 17 | 35 |
| PF# 963 | MNPFVKTARVAITSTLVAGSLATASLVFAPLAQA-DY<br>Gtgaatcccttcgtcaagacggcgcgcgtggctatcacctcgacgc<br>Tggtggcaggctcgctcgccactgccagcctcgtgtttgcaccactt<br>gcacaggccgattac | 18 | 36 |

Even more preferably, a nucleotide sequence coding for a signal peptide can be selected from the following sequences:
sequence SEQ ID NO: 18 encoding the signal protein of protein PF963 of *P. freudenreichii* (table I above);
the complementary sequence of same;
sequences at least 80% similar to same or to the complementary sequence of same; and
sequences at least 80% hybridizable in strict conditions with same or with the complementary sequence of same.

A nucleotide sequence that is "complementary" to a reference nucleotide sequence refers herein to any DNA whose nucleotides are complementary to those of the reference sequence, and whose orientation is reversed (the complementary sequence is thus an antiparallel sequence). Two "complementary" nucleotide sequences are thus such that each base of one is paired with the complementary base of the other, with the orientation of the two sequences being reversed. The complementary bases are A and T (or A and U in the case of RNA), and C and G.

A nucleotide sequence that is "similar" or "homologous" to a reference nucleotide sequence refers herein to a nucleotide sequence with a percent identity with the reference nucleotide sequence of at least roughly 80%, preferably at least roughly 85%, more preferably at least roughly 90%, even more preferably at least roughly 95%, even more preferably at least roughly 98%, wherein said percentage is purely statistical and the differences between the two nucleotide sequences can be distributed randomly over their entire length. Similar sequences can thus include variations related to mutations in the reference sequence, wherein said mutations correspond in particular to truncations, substitutions, deletions and/or additions of at least one nucleotide. Similar sequences can also include variations related to degeneration of the genetic code.

In particular, sequences "at least roughly X % similar" to a reference nucleotide sequence coding for a PB signal peptide refer to variants of this sequence, wherein said variants have, over their entire length, at least roughly X % of bases identical to those of the reference sequence. The identical bases can be consecutive in their entirety or only in part. The variants thus envisaged can be the same length as the reference nucleotide sequence, or a different length, as it acts as a signal peptide in a PB. Indeed, those persons skilled in the art know that the expression products of nucleotide sequences with a certain level of similarity (at least roughly X %) can nevertheless, taking into account degeneration of the genetic code on the one hand, and the preferential use of certain codons according to the host organisms (bacteria, yeasts, etc.) on the other, fulfill the same function. These expression products can themselves be identical or similar. Here, these expression products are functional signal peptides in PB.

The definition above can be extended to amino acids sequences, or peptide/protein sequences, at least roughly X % similar to a reference amino acid sequence. This case includes protein variants with, over their entire length, amino acids at least roughly X % similar to those of the reference sequence. Here again, the similar amino acids can be consecutive in their entirety or only in part. Peptide/protein variants can be the same length or a different length, given that, preferably, the biological function of the reference amino acid sequence is conserved.

The expression "similar amino acids" refers herein to amino acids with the same side-chain reactivity. Thus, polarity and comparable ionization properties are used by persons skilled in the art to define groups of similar amino acids. For example, it is useful to categorize aliphatic amino acids, namely glycine, alanine, valine, leucine and isoleucine, within the same group. Similarly, dicarboxylic amino acids, aspartic acid and glutamic acid are similar. Also, serine and threonine belong to the same group in that they both carry an esterifiable alcohol group. Additionally, lysine, arginine and histidine can be cited as similar basic amino acids, etc.

In all the definitions above, "X" equals 80. In particular, "X" equals 85, preferably 90, more preferably 95 and even more preferably 98.

A sequence that is "hybridizable in strict conditions" with a reference nucleotide sequence refers herein to a nucleotide sequence capable of hybridizing under temperature and ionic strength conditions suitable to maintain hybridization between two complementary fragments of DNA. The "strict hybridization conditions" are consistent with the classic definition known to those persons skilled in the art (Sambrook and Russell, 2001). "Strict hybridization conditions" are, for example, conditions that enable the specific hybridization of two single-stranded nucleotide sequences after at least one washing step as described below. The hybridization step can in particular be carried out at roughly 65° C. for 12 h in a solution comprising 6× SSC, 0.5% SDS, 5×Denhardt's solution and 100 µg nonspecific DNA (salmon sperm DNA, for example), or in any another solution of equivalent ionic strength. The following step, comprising at least one washing, is carried out, for example, at roughly 65° C. in a solution comprising at most 0.2×SSC and at most 0.1% SDS, or in any another solution of equivalent ionic strength. The parameters defining the hybridization conditions depend on the temperature (Tm) at which 50% of the paired strands separate. For sequences of more than 30 bases, the temperature (Tm) is calculated according to the formula: Tm=81.5+0.41*[% G+C]+16.6* Log(cation concentration)−0.63*[% formamide]−(600/number of bases). For sequences of less than 30 bases, the temperature (Tm) is defined by the following relationship: Tm=4*(number of G+C)+2*(number of A+T). The hybridization conditions can thus be adapted by those persons skilled in the art according to the size of the sequences used, their GC content and other parameters, as indicated in particular in the protocols described in Sambrook and Russell (2001).

In particular, "reference nucleotide sequences" and "reference amino acid sequences" from *P. freudenreichii* can be obtained from its genomic sequence that has been recently made available by the Inventors (Falentin et al., 2010, Plos One; Genbank accession No. FN806773).

Preferably, a signal peptide will be selected from:
sequences SEQ ID NO 19 to 36 (table I above) and 45 to 57 (see table II below);
sequences at least 80% similar to same; and
analogs and derivatives of same.

More preferably, said signal peptide will be selected from:
sequence SEQ ID NO 36 corresponding to the signal peptide of protein PF963 of *P. freudenreichii* (table I above);
sequences at least 80% similar to same; and
analogs and derivatives of same.

Table II below presents said amino acid sequences, identified by the Inventors from the genomic sequence of *P. acnes*, accessible from databases (strain *P. acnes* KPA171202; accession number: NCBI: NC_006085; GenBank: AEO17283).

TABLE II

| Protein sequence accession number | Putative sequence of the signal peptide | SEQ ID NO | Associated function | Homologous protein in *P. freudenreichii* |
|---|---|---|---|---|
| PPA2239 | MSKVVASAIA GALSTLSAGG LTMVQA | 45 | | PF1328 |
| PPA1840 | mrkaivtpva vlavlvmalt gcgqknqsgg | 46 | | PF1347 |
| PPA1786 | mastprrrwa wvlllvvasl vivgvyrka | 47 | | PF1885 |
| PPA2198 | mssmkglslv latsfmlsfs pgssfa | 48 | | PF2074 |
| PPA0721 | mehrygasqv sgsaprrgrg | 49 | | PF241 |
| PPA2198 | mssmkglslv latsfmlsfs pgssfas | 50 | | PF3412 |
| PPA0257 | mphsdqptsk rvmsaprrrm pgwvpvtvgi avvvivvvav ivsslrs | 51 | | PF876 |
| AAA51650 | mfgtpsrrtf ltasalsama laasptvtda ia | 52 | hyaluronidase | |
| CAA67627 | mkinarfavm aasvavlmaa apiaqa | 53 | triacylglycerol lipase | |
| AAT83976 | mypvhlplrn esefsfrahn hggtvpsrlt rrsvlatgav alpmtaaaca | 54 | lipoprotein | |
| AAT83859 | mrhmrplial slaglmtlsa cgedvaa | 55 | peptide-binding protein | |
| AAT83771 | mnrtlkvaav gaiailclaa csdpgsdsaq s | 56 | secreted sugar-binding protein | |
| AAT83059 | mekssfaaan mtimsepttp tsqa | 57 | secreted protease | |

In one embodiment, said nucleic acid sequence encoding a propionibacterial signal peptide can be selected from the group consisting of:
the sequences SEQ ID NO: 1 to 18, particularly the sequence SEQ ID NO: 18;
the nucleic acid sequences encoding the signal peptides of sequences SEQ ID NO: 45 to 57; and
the sequences having at least 80%, more particularly at least 85%, at least 86%, at least 87%, at least 88%, at least 89%, at least 90%, at least 91%, at least 92%, at least 93%, at least 94%, at least 95%, at least 96%, at least 97%, at least 98% and even more particularly at least 99% of identity with one of said sequences over the entire length of said sequence and corresponding to a peptide signal, in particular to a peptide signal allowing the secretion, in particular into the extracellular medium, of said peptide and/or protein of interest by a *propionibacterium*.

The percentage of identity to which reference is made in the presentation of the invention are determined on the basis of global alignment of sequences to be compared, that is to say, on an alignment of sequences over their entire length, using for example the algorithm of Needlman and Wunsch 1970. This sequence comparison can be done for example using the needle software by using the parameter "Gap open" equal to 10.0, the parameter "Gap Extend" equal to 0.5, and a matrix "BLOSUM 62". Software such as needle is available on the website ebi.ac.uk worldwide, under the name "needle".

Advantageously, said nucleic acid sequence encoding a propionibacterial signal peptide can be selected from the group consisting of:
the sequence of the signal peptide of a gene encoding a surface layer protein of a *Propionibacterium freudenreichii*;
the sequences having at least 80% more particularly at least 85%, at least 86%, at least 87%, at least 88%, at least 89%, at least 90%, at least 91%, at least 92%, at least 93%, at least 94%, at least 95%, at least 96%, at least 97%, at least 98% and even more particularly at least 99% of identity with said sequence over the entire length of said sequence and corresponding to a peptide signal, in particular to a peptide signal allowing the secretion, in particular into the extracellular medium, of said peptide and/or protein of interest by a *propionibacterium*.

Said surface layer protein can be selected from the group consisting of the surface layer protein A, the surface layer protein B, the surface layer protein C, the surface layer protein D, the surface layer protein E and the surface layer protein F of a *Propionibacterium freudenreichii*, in particular the surface layer protein A.

Unexpectedly, the Inventors have demonstrated that signal peptides of genes encoding a surface layer protein of a *Propionibacterium freudenreichii* allow the secretion into the extracellular medium of a peptide and/or a protein of interest by a *propionibacterium*. These results are really surprising since surface layer proteins are, as indicated by their name, described as proteins anchored in the surface of *Propionibacterium freudenreichii* (Lortal et al. 1993).

More surprisingly, the Inventors have shown that said signal peptides in combination with promoters of genes encoding a surface layer protein of a *Propionibacterium freudenreichii* allow the secretion into the extracellular medium of a peptide and/or a protein of interest by a *propionibacterium* at a level up to 100 times greater than that obtained with other signal peptides.

In one embodiment, the recombinant vector according to the invention for expressing and secreting, by a *propionibacterium*, at least one eukaryotic peptide or protein of interest, comprising at least:
under the control of at least one suitable promoter,
at least one nucleic acid sequence encoding a propionibacterial signal peptide and,
at least one nucleic acid sequence encoding said peptide or protein of interest;

wherein said at least one nucleic acid sequence encoding a propionibacterial signal peptide is translationally fused to said at least one nucleic acid sequence encoding said peptide or protein of interest; and wherein said promoter and said propionibacterial signal peptide are the promoter and the propionibacterial signal peptide of at least one gene encoding a surface layer protein of a *Propionibacterium freudenreichii*, in particular said surface layer protein being selected from the group consisting of the surface layer protein A, the surface layer protein B, the surface layer protein C, the surface layer protein D, the surface layer protein E and the surface layer protein F more particularly the surface layer protein A.

In one embodiment, said promoter and said propionibacterial signal peptide are the promoter and the propionibacterial signal peptide of the same gene encoding a surface layer protein of a *Propionibacterium freudenreichii*, In particular, said nucleic acid sequence encoding a propionibacterial signal peptide is selected from the group consisting of:
the nucleic acid sequences encoding the signal peptides of sequences SEQ ID NO: 59 to 68, in particular of sequence SEQ ID NO: 59;
the sequences having at least 80% of identity with one of said sequences over the entire length of said sequence and corresponding to a peptide signal, in particular a peptide signal allowing the secretion, particularly into the extracellular medium, of said peptide and/or protein of interest by a *propionibacterium*.

Unexpectedly, the inventors have demonstrated that the signal peptide having the sequence set forth in SEQ ID NO: 59 in combination with the promoter of the gene encoding the Surface layer protein A of a *Propionibacterium freudenreichii* allows the secretion into the extracellular medium of a peptide and/or a protein of interest by different strains of *Propionibacterium freudenreichii* at a level up to 100 times greater than that obtained with other signal peptides and promoters.

TABLE III

Sequences of the different signal peptides corresponding to surface layer (slp) genes identified in different strains of *Propionibacterium freudenreichii*

| Strain (CIRM BIA N°) | Gene name | Locus Tag | Product | Signal peptide | SEQ ID NO: |
|---|---|---|---|---|---|
| 118 | slpA | PFCIR M118_ 06465 | S-layer protein A | MATGAAAAMFVTTFAG MAPANA | 59 |
| 118 | slpB | PFCIR M118_ 02660 | S-layer protein B | MSVRKSLTGMALGLALTI TPLAGAVPASA | 60 |
| 118 | slpD | PFCIR M118_ 04435 | S-layer protein D | MRRFFSAAIAILLAATLTP ALNAPMASA | 61 |
| 121 | slpD | PFCIR M121_ 00945 | S-layer protein D | MRRFFSAAIAILLAATLTP ALNAPMASA | 62 |
| 122 | slpB | PFCIR M122_ 04010 | S-layer protein B | MSVRKSLTGMALGLALTI TPLAGAVPAAA | 63 |

TABLE III-continued

Sequences of the different signal peptides corresponding to surface layer (slp) genes identified in different strains of *Propionibacterium freudenreichii*

| Strain (CIRM BIA N°) | Gene name | Locus Tag | Product | Signal peptide | SEQ ID NO: |
|---|---|---|---|---|---|
| 122 | slpD | PFCIR M122_11375 | S-layer protein D | MRRFFSAAIAILLAATLTP ALNAPMASA | 64 |
| 122 | slpE | PFCIR M122_10825 | S-layer protein E | MKTRVRSRKPAAGLAGIA LFASGLSLMSTVASR | 65 |
| 125 | slpA | PFCIR M125_05685 | S-layer protein A | MATGAAAAMFVTTFAG MAPANA | 66 |
| 129 | slpA | PFCIR M129_13370 | S-layer protein A | MATGAAAAMFVTTFAG MAPANA | 67 |
| 512 | slpA | PFCIR M512_08945 | S-layer protein A | MATGAAAAMFVTTFAG MAPANA | 68 |

In one embodiment, the recombinant vector according to the invention comprises the nucleotide sequence SEQ ID NO: 69 translationally fused to said nucleic acid sequence encoding said peptide or protein of interest.

The nucleotide sequence SEQ ID NO: 69 comprises the promoter and the signal peptide of the Surface layer protein A of the *Propionibacterium freudenreichii* CIRM BIA 118 (CIRM: "Centre International de Ressources Microbiennes"; BIA: "Bactéries d'Intérêt Alimentaire").

A particularly preferred recombinant vector is obtained by inserting a nucleotide sequence encoding a peptide or protein of interest in vector pFB4 (contained in the recombinant strain *Escherichia coli* DH5α deposited with the *Collection Nationale de Cultures de Microorganismes* (CNCM, Institut Pasteur, 25 rue du Docteur Roux, 75724 Paris Cedex 15, France) on Apr. 15, 2010 and registered under number I-4297).

In the recombinant vector according to the invention, the propionibacterial signal peptide is "translationally fused" with the peptide or protein of interest, an essential condition so that it can be secreted by the host cell. In other words, in the recombinant vector according to the invention said at least one nucleic acid sequence encoding a propionibacterial signal peptide is translationally fused to said at least one nucleic acid sequence encoding said peptide or protein of interest.

It is observed that a signal peptide could be translationally fused with several amino acid sequences in a series, making it possible to express and secrete a chimeric protein, for example. Alternately or additionally, the same vector can possibly carry several translational fusions of a signal peptide and a peptide and/or protein of interest, under the control of one or more promoters. The promoters in question can control the transcription of only one or of several of these translational fusions.

In the context of the present invention, the peptide and/or protein of interest that will be expressed from the recombinant vector of the invention are preferably eukaryotic. In particular, they can be from animal origin, more preferably from mammalian origin. In particular, they can originate from mammals selected from rodents such as mice, rats, rabbits, Chinese pigs, hamsters; canidae (e.g., dogs) and felidae (e.g., cats); domestic livestock, including cows, pigs, goats, sheeps, horses; and humans. Even more preferably, the amino acid sequences of interest are from human origin.

Preferably, at least one eukaryotic peptide and/or protein of interest to be expressed and secreted using the recombinant vector according to the present invention has a chemical mediation activity.

Advantageously, any or all of the eukaryotic peptide and/or protein of interest to be expressed and secreted using the recombinant vector according to the present invention has(ve) a chemical mediation activity.

In other words, at least one of the peptide and/or protein of interest that will be expressed from the recombinant vector according to the present invention has a biological activity of interest, preferably a chemical mediation activity.

The terms and expressions "activity," "function," "biological activity," "biological function," "bioactivity," "(biological) activity of interest" and "(biological) function of interest" are equivalent and refer to a biological activity that is of interest, especially for medical purposes, such as an activity of chemical mediation. In particular, the peptide and/or protein of interest that will be expressed from the vector according to the present invention is "functional" or "active" or "bioactive," that is, it is able to fulfill its natural biological function, which is independent (from a qualitative and/or quantitative point of view) of post-translational modifications not able to be carried out by a *propionibacterium*.

Any eukaryotic protein whose biological activity is of interest to industry or medicine is thus within the scope of the present invention, insofar as said activity does not depend on post-translational modifications not able to be carried out by a *propionibacterium*.

The principal utility of the invention is to make it possible to produce an eukaryotic peptide and/or protein of interest. It is described here another utility of the invention that is to recycle industrial organic waste or residual by-products. Thus, for example, whey and molasses, which are produced as unused residues by certain industries, may be recycled as substrates for the culture of recombinant *propionibacterium* able to synthesize peptide and/or protein of interest.

An eukaryotic peptide or protein, or a fragment or domain thereof, having an activity of "chemical mediation" is a "chemical mediator", i.e., a peptide or protein naturally secreted by an eukaryotic cell, or a fragment or domain of such a peptide or protein, and that is capable of binding a cell receptor to induce a cellular response. Examples of chemical mediators include neuromediators or neurotransmitters, hormones, growth factors, cytokines, and the like. Chemical mediators also include fusion peptides or proteins capable of binding to a cell receptor.

Preferably, the eukaryotic peptide or protein of interest that can be expressed and secreted from the vector according to the invention, has a chemical mediation activity that is of medical interest such as an activity selected from proapoptotic, anti-inflammatory, immunomodulatory activities, and combinations thereof.

In other words, in one embodiment, said peptide or protein of interest can have a biological activity selected from the group consisting of proapoptotic activity, anti-inflammatory activity and immunomodulatory activity.

The peptide or protein of interest may be selected from cytokines, chemokines, peptide hormones, neurotransmitters, peptides involved in inflammation, satiety, blood pressure, etc. . . . The peptide or protein of interest is preferably a proapoptotic and/or anti-inflammatory peptide or protein, preferably from human origin. In particular, said peptide or protein of interest can be selected from the group consisting of:

a proapoptotic peptide or protein; and
an anti-inflammatory peptide or protein.

According to a preferred embodiment, the peptide or protein of interest is a cytokine.

The peptide of interest can be a biologically active fragment or domain of a protein of interest. This means that when the peptide of interest expressed from the vector according to the present invention is a protein fragment or domain, it remains "functional" or "active" or "bioactive," that is, it is able to fulfill the natural biological function of the corresponding native protein. All definitions provided herein with respect to proteins also apply to biologically active fragments or domains thereof.

In a preferred embodiment, the recombinant vector according to the present invention makes it possible to express and secrete the proapoptotic TRAIL protein (TNF-related apoptosis-inducing ligand, also called TNSF10, TL2, CD253 and Apo-2L), a cytokine of the TNF family. The sequence of the *Homo sapiens* TRAIL protein can be the sequence set forth in SEQ ID NO: 58 (accession number AAC50332.1). In particular, the amino acid sequence of interest is that of the active C-terminal extracellular domain of TRAIL, preferably the sequence from amino acids 114 to 281 of TRAIL (TRAIL sequence accession number in GenBank: U37518; Uniparc: UPI0000001629).

Thus, in one embodiment, said peptide or protein of interest can be the proapoptotic TRAIL protein or the C-terminal extracellular domain of the TRAIL protein, in particular the *Homo sapiens* proapoptotic TRAIL protein or the C-terminal extracellular domain of the *Homo sapiens* TRAIL protein.

In particular, said nucleic acid sequence encoding said peptide or protein of interest can be the sequence from amino acids 114 to 281 of the TRAIL protein sequence set forth in SEQ ID NO: 58.

According to the literature, TRAIL is an antineoplastic agent with strong potential because it induces the death of many tumor cells, independently of p53 and Pgp180 (MDR, multidrug resistance). TRAIL also inhibits the growth of xenografted colon tumors in nude mice (Ashkenazi et al., 1999). Quite interestingly, TRAIL has little cytotoxic effect on most normal tissues (Ashkenazi et al., 1999), including human colon epithelium (Sträter et al., 2002).

Other teams very recently expressed the active C-terminal extracellular domain of TRAIL in bacteria such as *Salmonella typhimurium* (Ganai et al., 2009), *Bifidobacterium longum* (Hu et al., 2009) and *E. coli* (Zhang et al., 2010). In this work, salmonellas, bifidobacteria and coliform bacteria are proposed as systemic TRAIL delivery vectors in cancer models.

However, propionibacteria have major advantages compared to other bacteria such as salmonellas, bifidobacteria and coliform bacteria.

First, dairy propionibacteria enable local delivery because they target colon epithelial cells and have an active fermentative metabolism in the human colon (Hervé et al., 2007), which enables site-specific delivery of TRAIL.

Second, dairy propionibacteria themselves have proapoptotic properties. It was recently shown in vitro that dairy propionibacteria, by the SCFA resulting from their fermentative metabolism, induce the apoptosis of two human colon adenocarcinoma cell lines (Caco2 and HT29) (Jan et al., 2002). This effect is directly related to the release of propionate by these bacteria and to their action on cancer cell mitochondria. It has also been shown that at extracellular pH ($pH_e$) between 6 and 7.5, SCFA (propionate and acetate SCFA) induce apoptotic death whereas at $pH_e$=5.5, they induce necrotic death in HT29 human colon cancer cells (Lan et al., Apoptosis, 2007). In vivo, these food-quality (GRAS: generally regarded as safe) bacteria adapt and survive in the digestive tract of animals and humans with an efficiency that, although strain-dependent, exceeds that of other probiotics (Hervé et al., 2007). Moreover, they express in the intestine enzymatic activities characteristic of their fermentative metabolism by producing an increase in SCFA concentrations (Lan et al., Br. J. Nutr., 2007) and induce an increase in apoptosis in the mucosa of the colon of rats treated with 1,2-dimethylhydrazine (Lan et al., 2008). The Inventors have further shown a synergistic action with TRAIL in vitro as illustrated in the examples below.

A particularly preferred recombinant vector is the vector pFB4:TRAIL, wherein the amino acid sequence of interest is the sequence from amino acids 114 to 281 of the TRAIL C-terminal extracellular domain. This vector is hosted by type strain CIP103027 of *P. freudenreichii* subsp. *shermanii*, deposited on Jul. 23, 2009 under number I-4213 with the Collection Nationale de Cultures de Microorganismes (CNCM, Institut Pasteur, 25 rue du Docteur Roux, 75724 Paris Cedex 15, France).

Another particularly preferred recombinant vector is the vector pCHH04: TRAIL wherein the peptide of interest is the sequence from amino acids 114 to 281 of the TRAIL C-terminal extracellular domain, said sequence being translationally fused to the signal peptide of the Surface layer protein A of the *Propionibacterium freudenreichii* CIRM BIA 118, under the control of the promoter of the Surface layer protein A of the *Propionibacterium freudenreichii* CIRM BIA 118. A *P. freudenreichii* CIRM-BIA-118 comprising said vector pCHH04: TRAIL has been deposited on Nov. 13, 2012 under number CNCM I-4692 with the Collection Nationale de Cultures de Microorganismes (CNCM, Institut Pasteur, 25 rue du Docteur Roux, 75724 Paris Cedex 15, France).

The present invention further relates to a recombinant *propionibacterium* comprising at least one recombinant vector according to the invention as previously defined.

The *propionibacterium* comprising at least one recombinant vector according to the invention can be selected in the group consisting of *P. freudenreichii*, *P. jensenii*, *P. thoenii*, *P. acidipropionicii*, *P. acnes*, *P. granulosum*, *P. avidum*, *P. propionicum* and *P. microaerophilum*.

In particular, the *propionibacterium* comprising at least one recombinant vector according to the invention can be a *P. freudenreichii* selected in the group consisting of *P. freudenreichii* freudenreichii and *P. freudenreichii* shermanii.

Advantageously, the *propionibacterium* comprising at least one recombinant vector according to the invention can be a *P. freudenreichii*, in particular chosen in the group consisting of CIRM BIA 512 strain, CIRM BIA 125 strain, CIRM BIA 118 strain, CIRM BIA 129 strain and CIRM BIA 122 strain, more particularly CIRM BIA 512 strain, CIRM BIA 125 strain, CIRM BIA 118 strain and CIRM BIA 129 strain, even more particularly CIRM BIA 512 strain, CIRM BIA 125 strain, CIRM BIA 118 strain and even more particularly CIRM BIA 512 strain and CIRM BIA 118 strain and even more particularly CIRM BIA 118 strain.

Advantageously, the recombinant vector will be carried by the chromosome of the *propionibacterium* according to the invention. The vector can be integrated, for example, in the chromosome of the host cell by homologous recombination.

One particularly preferred *propionibacterium* is type strain CIP103027 of *P. freudenreichii* subsp. *shermanii*, deposited with the CNCM on Jul. 23, 2009 under number I-4213.

Another particularly preferred *propionibacterium* is the *propionibacterium* deposited on Nov. 13, 2012 under number CNCM I-4692 with the *Collection Nationale de Cultures de Microorganismes* (CNCM, Institut Pasteur, 25 rue du Docteur Roux, 75724 Paris Cedex 15, France).

If the peptide or protein of interest to be secreted lends itself to such a use (an anorexiant peptide, for example), the *propionibacterium* according to the invention could be used as a probiotic food or dietary supplement for mammals, in particular humans. Advantageously, the *propionibacterium* will be integrated in the mammal's food in the form of a fermented dairy product (e.g., fermented milk, fermented whey, cheese).

The present invention further relates to a recombinant vector or a recombinant *propionibacterium* as defined above, for the use of same as a drug.

In other words, the invention also relates to a recombinant vector or a recombinant *propionibacterium* according to the invention, for its use as a drug, in particular for the prevention and/or treatment of a disease, in particular cancer and more particularly colorectal cancer.

The present invention further relates to a drug (or pharmaceutical composition) comprising an effective quantity (amount) of at least one vector according to the invention and/or at least one *propionibacterium* according to the invention and at least one pharmaceutically acceptable carrier (or excipient).

Such therapeutically effective amount can be determined by one skilled in the art by routine tests including assessment of the effect of administration of said components (vector according to the invention and/or *propionibacterium* according to the invention) on the pathologies and/or disorders which are sought to be prevent and/or to be treated by the administration of said drug (or pharmaceutical composition).

For example, such tests can be implemented by analyzing both quantitative and qualitative effect of the administration of different amounts of said aforementioned components (vector according to the invention and/or *propionibacterium* according to the invention) on a set of markers (biological and/or clinical) characteristics of said pathologies and/or of said disorders, in particular from a biological sample of a subject.

In said drug, the vector and/or the *propionibacterium* of the invention are advantageously used as therapeutic agents. A drug according to the invention can be manufactured in a conventional way. A drug in accordance with the invention can moreover include one or more pharmaceutically acceptable excipients or additives such as diluents, adjuvants, anti-foaming agents, stabilizers, dispersants, colorants, preservatives, etc. Inert excipients or adjuvants can be used in such a way that, in the drugs according to the present invention, the only therapeutic agents will be the vector and/or the *propionibacterium*. Nevertheless, the drug according to the present invention can include one or more other therapeutically or prophylactically active agents, in addition to the vector and/or the *propionibacterium*. Advantageously, the combination of several therapeutic agents, including at least the vector and/or the *propionibacterium*, will have a better therapeutic or prophylactic action than when the vector and/or the *propionibacterium* are the only therapeutic agents present in the drug. This better action can be, among others:

a better dose-effect relationship;
a therapeutic or prophylactic effect that is more stable or longer lasting over time;
a better administration of the drug;
a synergy of action between at least two therapeutic agents present in the drug.

Preferably, a drug in accordance with the present invention is intended to prevent and/or to treat at least one disease selected from allergies, hypertension (e.g., the peptide or protein of interest has a hypotensive activity), obesity (e.g., the peptide or protein of interest has an anorexiant activity), cancers, in particular colorectal cancers (e.g., the peptide or protein of interest has a proapoptotic activity) and inflammatory colon diseases, in particular Crohn's disease (wherein the peptide or protein of interest is advantageously an anti-inflammatory cytokine, for example IL-10), etc. . . .

Alternately, a drug of the invention is intended to prevent at least one microbial infection, for example a viral, bacterial, fungal or parasitic infection, etc. In this case, the peptide or protein of interest will be an antigen or an epitope, for example. Thus, said drug advantageously will be a vaccine, in which case the pharmaceutically acceptable carrier could be an immune adjuvant.

The various means of the present invention (vector, *propionibacterium*, drug) as described above are preferably administered to a mammal for the secretion of the peptide and/or protein of interest in the small intestine and/or the colon, preferably the colon, of said mammal.

The term "mammal" is defined in its usual sense. Examples of mammals include bovines; pigs; goats; sheep; horses; rodents such as mice, rabbits, rats and hamsters; felines and canines, including domestic animals such as cats and dogs. A preferred mammal in the context of the invention is a human.

The means of the invention (vector, *propionibacterium*, drug) can be administered by any suitable conventional route, in particular selected from the oral, subcutaneous, intramuscular, intravenous, intrarectal, enema and intratracheal routes. Oral administration is preferred, wherein the drug is in the form of tablets, hard gelatin capsules (e.g., gastroprotective gelatin capsules), soft capsules, powders for direct use or for dilution (e.g., lyophilisates), syrups, gels, etc. Said means can be administered in a single or repeated dose one or more times spaced over a certain interval of time. The suitable administration route and dosing schedule can vary according to various parameters, such as the subject to be treated and/or the peptide and/or protein of interest.

The invention further relates to a method of therapeutic or prophylactic treatment, wherein a therapeutically effective quantity of a vector and/or a *propionibacterium* and/or a drug according to the invention is administered to a subject in need of such a treatment.

In other words, the invention also relates to a method for therapeutic or prophylactic treatment of a subject in need thereof, comprising the step of administering to said subject a therapeutically effective amount of at least one compound selected from the group consisting of:

a vector according to the invention;
a *propionibacterium* according to the invention; and
a drug according to the invention.

The invention also relates to a method for therapeutic or prophylactic treatment of a disease, in particular a cancer, more particularly a colorectal cancer, comprising the step of administering to a subject in need thereof a therapeutically effective amount of at least one compound selected from the group consisting of:
- a vector according to the invention;
- a *propionibacterium* according to the invention; and
- a drug according to the invention;

wherein the peptide or protein of interest is the proapoptotic TRAIL protein or the C-terminal extracellular domain of the TRAIL protein (in particular having the sequence from amino acids 114 to 281 of the protein TRAIL sequence set forth in SEQ ID NO: 58).

The present invention further relates to the use of a vector and/or a *propionibacterium* in accordance with the preceding description to produce and secrete, preferably into the extracellular medium, one or more peptides and/or proteins of interest.

The present invention further relates to a method for producing and secreting into the extracellular medium, by a *propionibacterium* according to the invention, at least one amino acid sequence of interest (at least one peptide or protein of interest) as defined above, wherein said method comprises at least:
- culturing said *propionibacterium* under suitable conditions;
- recovering the culture medium containing said amino acid sequence of interest (said peptide or protein of interest) (since it is secreted in the culture medium by the *propionibacterium*); and
- optionally, purifying said amino acid sequence of interest (said peptide or protein of interest).

Preferably, the method according to the invention makes it possible to produce and secrete peptides and/or proteins on a large scale, that is, on an industrial scale (in protein production plants).

The "suitable conditions" (in terms of the composition of the culture medium, temperature, time, ventilation, stirring, etc.) for culturing propionibacteria are known to those persons skilled in the art (see in particular documents US 20090312425 in the name of Meiji Dairies Corp. and CN 101045910 in the name of Nanjing University of Technology). Once again, these bacteria are robust, are able to grow on particular substrates such as whey or molasses and are able to adapt to non-standard culture conditions, characteristics which a large number of other bacteria do not share.

Peptide, protein purification calls upon the general knowledge of those persons skilled in the art and can be carried out without any difficulty using classic techniques.

The invention further relates to pharmaceutical products containing at least one *propionibacterium*, preferably one non-recombinant *propionibacterium*, and at least one peptide or protein of interest as a combination product for prophylactic or therapeutic use, in mammals, that is simultaneous, separated or sequential over time.

The invention also relates to a combination product, which comprises:
- at least one vector according to the invention and/or at least one *propionibacterium* comprising said vector; and
- at least another active agent, in particular chosen in the group consisting of an anti-tumoral agent, an anti-inflammatory agent and immunomodulatory agent, more particularly an anti-tumoral agent;
for simultaneous, separate or sequential use a medicament.

Said active agent can be a short-chain fatty acid (SCFA), preferably propionate or acetate.

The pharmaceutical products according to the invention can comprise the peptide or protein itself or a nucleotide sequence encoding said peptide or protein, wherein said nucleotide sequence is optionally carried by a suitable expression vector.

For example, the pharmaceutical products in accordance with the present invention are intended to prevent and/or to treat at least one disease selected from allergies, hypertension (e.g., the peptide or protein of interest has a hypotensive activity), obesity (e.g., the peptide or protein of interest has an anorexiant activity), colorectal cancers (e.g., the peptide or protein of interest has a proapoptotic activity) and inflammatory colon diseases, in particular Crohn's disease (wherein the peptide or protein of interest is advantageously an anti-inflammatory cytokine, for example IL-10), etc. Alternately, said products can be intended to prevent at least one microbial infection, for example a viral, bacterial, fungal or parasitic infection, etc. In this case, the peptide or protein of interest will be an antigen or an epitope, for example.

Advantageously, for an antineoplastic therapy, in particular for the treatment of colorectal cancers, the pharmaceutical products according to the present invention preferably comprise:
- at least one non-recombinant *propionibacterium* such as *P. freudenreichii*, in particular subsp. *shermanii*, and
- at least the TRAIL protein or the peptide of sequence from amino acids 114 to 281 of the TRAIL C-terminal extracellular domain, in particular set forth in SEQ ID NO: 58.

In said pharmaceutical products, the *propionibacterium* can be administered in the form of a probiotic which will be added to the mammal's food and which will serve, for example, as an adjuvant TRAIL-based chemotherapy. In the latter case, it is recalled that, as being typically administered systemically, conventional chemotherapeutic treatments have a lot of undesirable side-effects, in particular due to a high dosage regime and a lack of specificity. Thus, by orally administering the probiotic *propionibacterium* as an adjuvant to a TRAIL-based chemotherapy, the bacteria and TRAIL will be able to exhibit an enhanced, advantageously synergistic, anti-tumoral activity in the colon, resulting in noticeably reduced (or even prevented) side-effects by reducing the required dosages and increasing the specificity of the treatment.

Alternatively, still in reference to an antineoplastic therapy, in particular for the treatment of colorectal cancers, the pharmaceutical products according to the present invention comprise:
- a culture supernatant of a non-recombinant *propionibacterium* such as *P. freudenreichii*, in particular subsp. *shermanii*, wherein said supernatant has optionally undergone one or more suitable conventional treatments to improve its harmlessness and/or preservation and/or physicochemical properties etc., and
- at least the TRAIL protein or the peptide of sequence from amino acids 114 to 281 of the TRAIL C-terminal extracellular domain, in particular set forth in SEQ ID NO: 58.

As the examples illustrate below, the Inventors indeed have shown a synergy of proapoptotic action on HT29 colon cancer cells between *propionibacterium* and/or *propionibacterium* culture supernatants (containing SCFA, in particular propionate and/or acetate SCFA) and TRAIL.

Alternately again, and still in reference to an antineoplastic therapy, in particular for the treatment of colorectal cancers, the pharmaceutical products according to the present invention comprise:

one or more SCFA, in particular propionate and/or acetate SCFA, advantageously obtained from the culture supernatant of one or more non-recombinant *propionibacterium* such as *P. freudenreichii*, in particular subsp. *shermanii*, and at least the TRAIL protein or the peptide of sequence from amino acids 114 to 281 of the TRAIL C-terminal extracellular domain, in particular set forth in SEQ ID NO: 58.

The invention further concerns a method for treating a cancer in a mammal in need thereof, comprising administering to said mammal:

at least one short-chain fatty acid (SCFA), preferably propionate and/or acetate, advantageously obtained by fermentation of at least one *Propionibacterium* such as *Propionibacterium freudenreichii*, and proapoptotic TNF-related apoptosis inducing ligand (TRAIL/Apo-2 ligand), or a functional fragment thereof.

Said mammal is as defined above.

Said cancer is preferably a colorectal cancer.

Said functional fragment of TRAIL preferably comprises amino acid sequence from position 114 to position 281 of the TRAIL C-terminal extracellular domain, in particular set forth in SEQ ID NO: 58.

Said SCFA and said TRAIL or functional fragment thereof may be administered to said mammal simultaneously, separately or sequentially.

The present invention is illustrated by the following figures:

FIG. 1: Graphs illustrating the synergy observed in vitro between TRAIL and *P. freudenreichii* metabolites. HT29 colon cancer cells were treated with sublethal doses of TRAIL (25 ng/ml, 50 ng/ml and 100 ng/ml). Various doses of SCFA (propionate/acetate SCFA, FIG. 1A) or of *P. freudenreichii* supernatant (FIG. 1B) were used in co-treatment. Viability of the HT29 cells was determined after 24 hours of treatment.

FIG. 2: Identification of the protein secreted in the majority by *P. freudenreichii*, PF963. A: growth of two strains of *P. freudenreichii*, one autolytic (□) and the other nonlytic (○). B and C: electrophoretic analysis (SDS-PAGE) of proteins secreted by a strain of lytic (B) and nonlytic (C)*P. freudenreichii*. Protein PF963 was identified by mass spectrometry.

Figure 3:
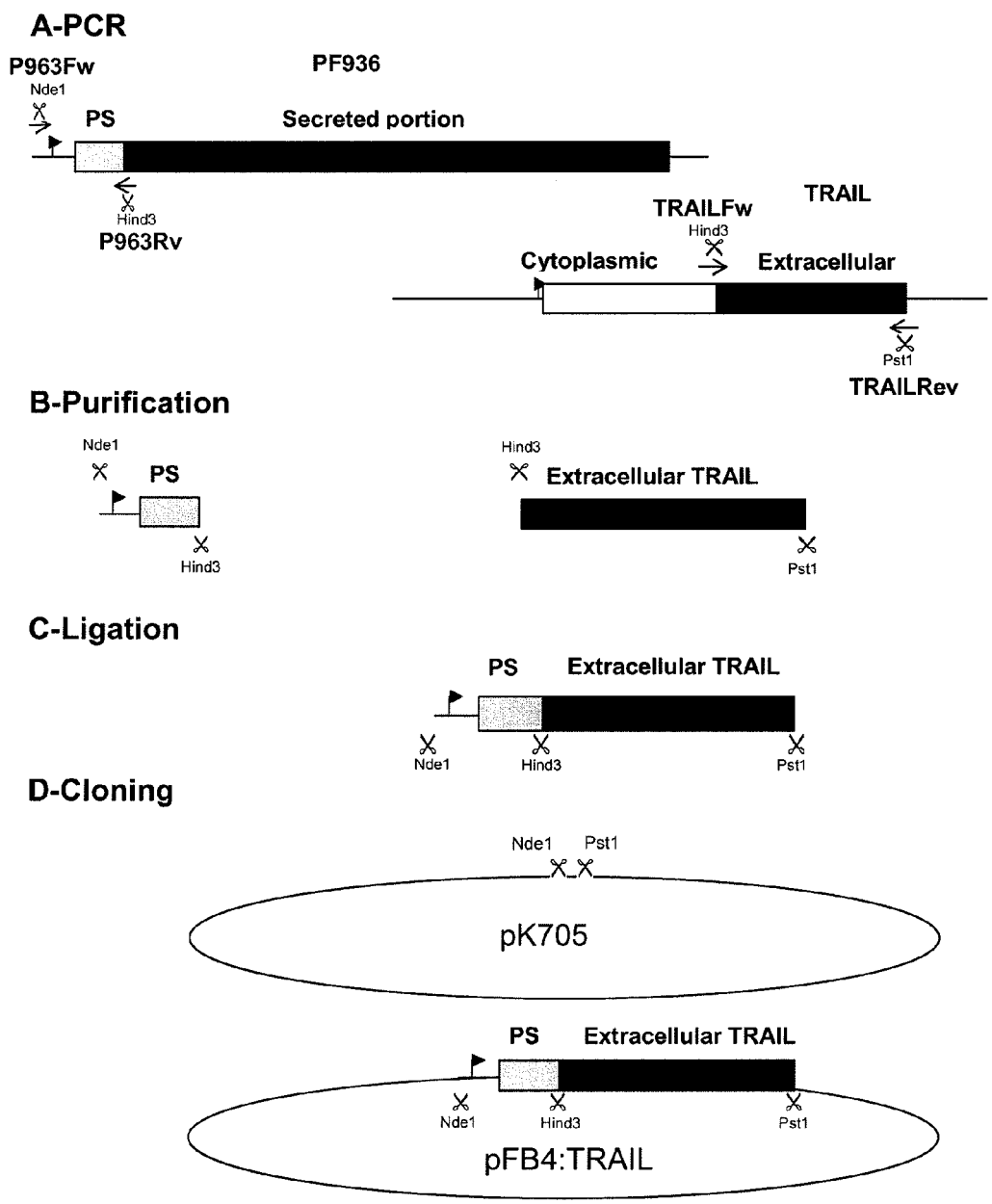

FIG. 3: Diagram detailing the cloning strategy to obtain the pFB4:TRAIL plasmid (deposited with the CNCM on Jul. 23, 2009 under number I-4213). A: the promoter region and signal peptide of the *P. freudenreichii* protein PF963 were amplified by PCR with introduction (PCR mutagenesis) of restriction sites NdeI and HindIII. The active extracellular portion of TRAIL (residues 114 to 281) was amplified by PCR with introduction of restriction sites HindIII and PstI. B and C: the two PCR products were purified and linked in order to obtain the ligation product SP-TRAIL. D: plasmid pK705 was opened by digestion using two enzymes NdeI and PstI. The ligation product SP-TRAIL was introduced into the open plasmid. The new plasmid pFB4 includes a promoter and a signal peptide enabling the secretion, in particular into the extracellular medium, by *P. freudenreichii* of a heterologous protein. The arrows and the scissors represent PCR primers and restriction sites, respectively.

Figure 4:
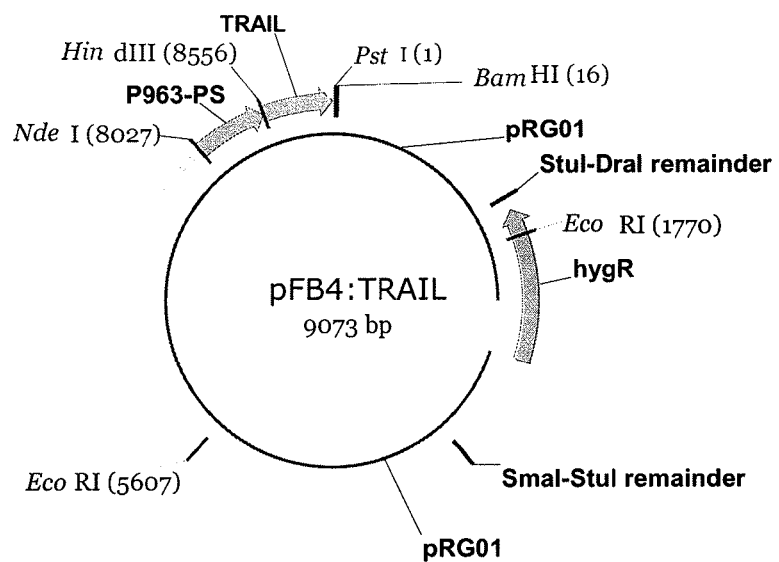

FIG. 4: Map of the pFB4:TRAIL plasmid (deposited with the CNCM on Aug. 13, 2009 under number I-4213).

FIG. 5: Sequence of the fusion protein (SEQ ID NO: 43) coded for by the pFB4:TRAIL plasmid (nucleotides 8451-9073 of SEQ ID NO: 42). In this sequence, the underlined region corresponds to the PF963 protein signal sequence and the region in bold corresponds to the TRAIL extracellular domain sequence (residues 114 to 281 of SEQ ID NO: 58).

Figure 6:
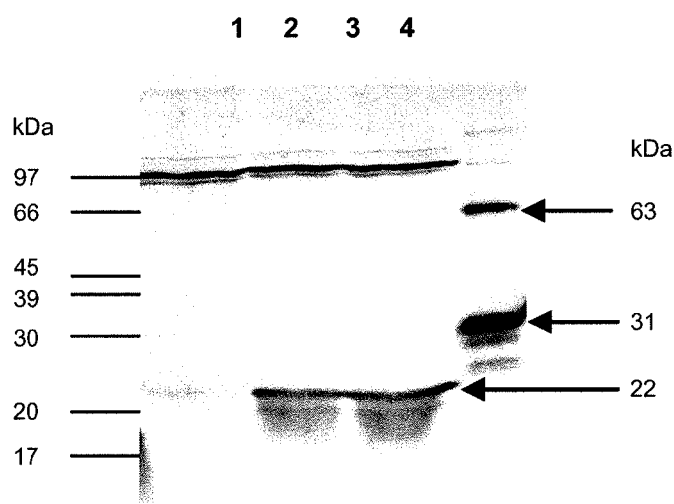

FIG. 6: Detection by Western blot of the fusion protein coded for by the pFB4:TRAIL plasmid. The samples deposited were culture supernatants of wild *P. freudenreichii* CIP103027 (1) or of *P. freudenreichii* CIP103027 carrying the pFB4:TRAIL plasmid (2 and 3). A solution of Super-KillerTRAIL™ (Alexis Biochemicals, Coger, France) was deposited as positive control (4). The Western blot was developed using a commercial "PAb to TRAIL" antibody (Alexis Biochemicals).

Figure 7:
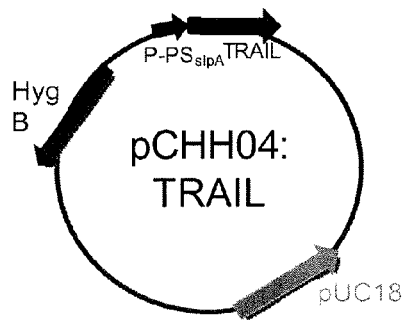

FIG. 7: Map of the pCHH04: TRAIL plasmid (deposited with the CNCM on Nov. 13, 2012 under number CNCM I-4692).

Figure 8:
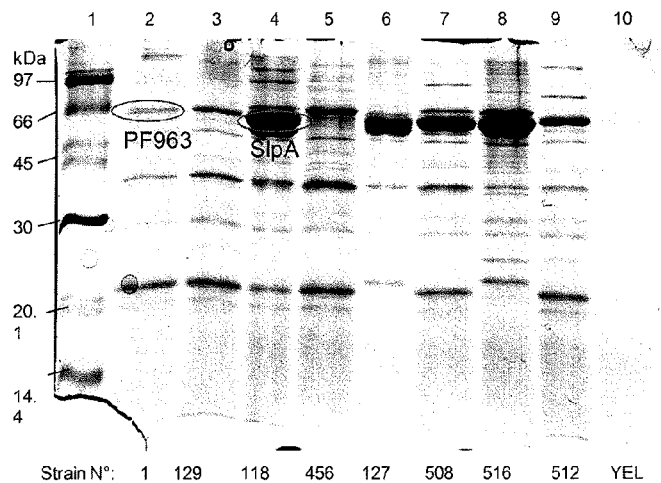

FIG. 8: Proteomic comparative analysis of *Propionibacterium freudenreichii* exoproteomes. Strains CIRM BIA 1, 129, 118, 456, 127, 508, 516 and 512 were grown in YEL medium and the culture supernatants analyzed by SDS PAGE followed by Coomassie Blue staining. The reference strain CIRM BIA 1, the first sequenced in 2010, secretes 4 proteins with equivalent efficiency, including PF963. Other strains, sequenced since then (unpublished data), secrete a major extracellular 60 kDa protein abundantly. This was identified in strain 118 as SlpA.

Figure 9:
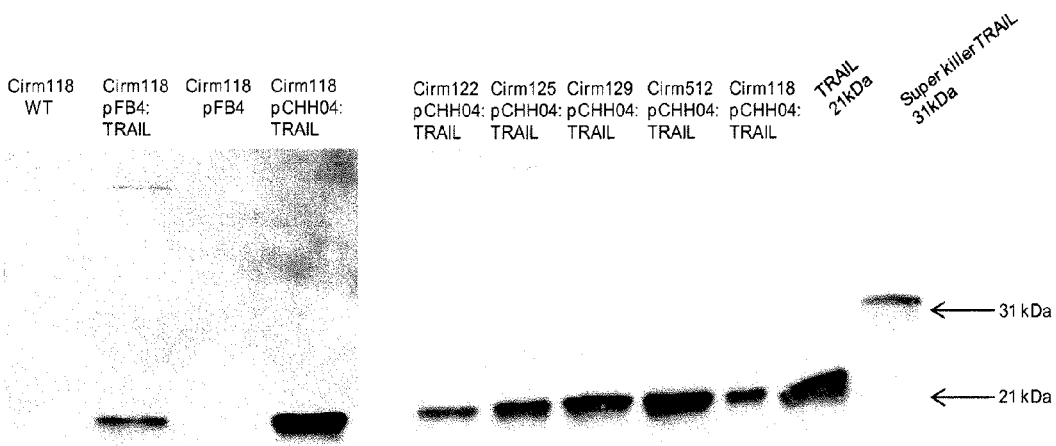

FIG. 9: Western Blot detection. The plasmids pFB4:TRAIL and pCHH04:TRAIL are compared within the same CIRM BIA 118 strain with respect to TRAIL secretion into the extracellular medium. Secretion of TRAIL into the extracellular medium is then compared in different strains harboring the pCHH04:TRAIL plasmid:The pCHH04:TRAIL plasmid was transformed into different strains of *Propionibacterium freudenreichii* and the resulting supernatants were analyzed with respect to TRAIL secretion by western blotting.

The following non-limiting examples, which refer to the figures above, illustrate the embodiments and advantages of the present invention.

EXAMPLES

I-Induction of the Intrinsic Mitochondrial Pathway of Apoptosis by *Propionibacterium freudenreichii*

During preliminary studies, the Inventors showed that certain selected strains of *P. freudenreichii* surviving the stresses undergone during intestinal transit in humans (Hervé et al., 2007), as well as in the rat (Lan et al., *Br. J. Nutr.* 2007), express the genes coding for fermentative metabolism enzymes and produce propionate and acetate short-chain fatty acids (SCFA) in situ in the colon (Lan et al., *Apoptosi* 2007).

Furthermore, this bacterium induced the apoptosis of human colon adenocarcinoma cells in vitro via these SCFA which act on cancer cell mitochondria (Jan et al., 2002). The mitochondrial pathway of apoptosis induction has been clearly identified in the triggering of programmed cell death of HT29 cells by dairy propionibacteria (Jan et al., 2002; Lan et al., 2007). Said SCFA cause the opening of mitochondrial permeability transition pores (PTP), the depolarization of mitochondria, the leaking of proapoptotic mitochondrial proteins and the activation of effector caspases.

Such an induction of apoptosis was then researched in vivo in a rat model of human digestive flora. Rats were treated or not treated by the carcinogen dimethylhydrazine (DMH) for the purpose of causing the appearance of damaged colonic epithelial cells likely to develop into colon cancer. These rats received by gavage, or did not receive, the *P. freudenreichii* bacterium. Colonic epithelial cell apoptosis and proliferation were quantified by anatomopathological analysis of histological sections of colon. The administration in healthy rats of *P. freudenreichii* had no effect on these parameters. On the other hand, a significant increase in apoptosis was observed in the rats treated with DMH (Lan et al., 2008). It thus appears that a specific apoptosis of cancer cells can be induced by dairy propionibacteria.

II-Induction of the Extrinsic Pathway of Apoptosis by TRAIL Via Death Receptors, Synergy with *Propionibacterium freudenreichii*

TRAIL is a cytokine capable of inducing the apoptosis of human colon cancer cells by binding to death receptors. TRAIL thus induces a different apoptotic pathway on the cellular and molecular levels and potentiates the action of other proapoptotic molecules used in cancer chemotherapy (Lacour et al., 2001; Lacour et al., 2003; Meurette et al., 2005; Meurette et al., 2006). Cell death induced by TRAIL or by SCFA is promoted by an acidic environment (Meurette et al., 2007; Lan et al., 2007).

By viability tests (FIG. 1), and by in vitro apoptosis quantification methods (Hoechst staining and caspases activity, data not shown), the Inventors showed a synergistic proapoptotic effect of the cytokine TRAIL in combination with the propionate/acetate mixture or the propionibacteria culture supernatant in HT29 human colon cancer cells (FIG. 1). More precisely, the viability illustrated in FIG. 1 was determined using the following cytotoxicity test. HT29 human colon cancer cells (ATCC, Biovalley) were cultured in 96-well plates (30,000 cells/well) for 24 hours. They were then treated with TRAIL (0 ng/ml, 25 ng/ml, 50 ng/ml and 100 ng/ml) (SuperKillerTRAIL™, Alexis Biochemicals, Coger, France) in the presence of increasing concentrations of propionate/acetate (7.5 mmol/3.5 mmol; 15 mmol/7.5 mmol; 30 mmol/15 mmol; 60 mmol/30 mmol) or of bacterial supernatant (*P. freudenreichii* bacteria) (⅙, ¼, ½, pure). At the end of treatment (24 hours), the medium was discarded and the adherent cells were washed three times with 1× PBS (100 µl/well) and fixed in 99% ethanol (100 µl/well) for 30 minutes. After discarding the ethanol, the fixed cells were air dried and then stained for 30 minutes with methylene blue (diluted in 1× borate buffer). After three washings in water and drying (roughly 30 minutes), 100 µl of hydrochloric acid (0.1 N) was added to the wells. The plates were then analyzed by spectrophotometer at a wavelength of 620 nm (iEMS Reader MF; Lab-systems, Helsinki, Finland).

FIG. 1 shows that sublethal doses of TRAIL (25 ng/ml, 50 ng/ml and 100 ng/ml) do not significantly induce cell death during the treatment period. Moreover, the smallest doses of SCFA alone induce little or no cell death, but induce massive death in the presence of TRAIL (FIGS. 1A and 1B). These results show a synergy of proapoptotic action on human colon cancer cells between SCFA metabolites produced by PB and TRAIL.

III-Development of a First Recombinant *Propionibacterium* with the Goal of Inducing Both the Intrinsic and Extrinsic Apoptotic Pathways III.1 Summary The Inventors sought to make a bacterium, harmless to healthy cells, produce inducers of the two apoptotic pathways. These inducers are the SCFA produced by *P. freudenreichii* for the intrinsic pathway and TRAIL for the extrinsic pathway. Since propionibacteria have a positive tropism for the mucosa of the colon, said recombinant bacterium will not only be likely to produce TRAIL in situ in the colon, but also to carry SCFA and TRAIL toward colon epithelial cells.

To this end, a recombinant *propionibacterium* expressing TRAIL fused with a secretion signal peptide was developed for in situ production in experimental models of cancer colon.

Briefly, the major protein secreted by *P. freudenreichii* during its growth and in the absence of lysis, named PF963, was identified. The experimental procedure (e.g., electrophoresis, trypsinolysis, nano-LC and MS/MS) which led to the identification of PF963 is similar to that which had previously enabled the Inventors to identify GAPDH (Tarze et al., 2007). Very briefly, the supernatant of the nonlytic strain of *P. freudenreichii* was analyzed by electrophoresis. The gel fragment containing the major protein secreted was removed, rinsed and then subjected to "in gel" trypsin proteolysis. The resulting peptides were separated by nano-LC and then analyzed with tandem mass spectrometry (MS/MS).

PF963 is an enzyme secreted via the machinery of the "Sec" pathway which recognizes and cleaves a signal peptide (SP). By genetic engineering, said SP was fused with the active C-terminal extracellular domain of TRAIL. This construction was carried out in *E. coli* on a cloning plasmid. The fusion thus obtained was introduced into an expression vector (pK705) previously developed for the cloning and expression of propionibacterial genes in dairy propionibacteria and efficient in *P. freudenreichii* (Kiatpapan et al., 2000) in order to express the fusion protein. The expression and the extracellular addressing of the fusion protein were then analyzed by Western blot.

According to FIG. 2A, the growth of *P. freudenreichii* shows that certain strains are lysed (□) and others not (○). In the latter case, protein PF963 is secreted in the medium (FIG. 2C) without leakage of cytoplasmic proteins as in the case of spontaneous bacterial lysis (FIG. 2B). The upstream portion of the PF963 gene, comprising the promoter and the signal peptide, was amplified by PCR and fused with the C-terminal portion of TRAIL (FIGS. 3A to 3C). The following step consisted of its introduction in a *P. freudenreichii* expression plasmid (FIG. 3D).

III.2 Obtaining the Strain *Propionibacterium freudenreichii* Subsp. *Shermanii* CIP103027 (TL34) Carrying the pFB4:TRAIL Plasmid.

III.2.1 Identification of the Protein PF963 Secreted by *Propionibacterium freudenreichii* Subsp. *Shermanii*.

In order to identify a secreted protein, strains were screened on the basis of aptitude for autolysis. Indeed, it is known that certain strains of said bacterium make use of a programmed cell suicide, autolysis. In this case, cytoplasmic proteins are released in the surrounding medium. On the other hand, other strains, including strain CIP103027, do not undergo autolysis and on the contrary make use of a tolerance reaction with respect to various stresses, called the starvation-induced multi-tolerance response. In principle, these nonlytic strains thus only release actively secreted proteins and do not release proteins by accident. FIG. 2A shows the evolution of the bacterial population for an autolytic strain (□) and for a nonlytic strain (○) of *Propionibacterium freudenreichii* subsp. *shermanii*.

FIG. 2C shows the electrophoretic analysis (SDS-PAGE) of proteins secreted by a nonlytic strain, CIP103027. This analysis reveals several secreted proteins, including protein PF963, identified in the culture supernatant of all the nonlytic strains tested. This protein was cut out of a preparative SDS-PAGE gel and subjected to digestion by trypsin. The resulting peptides were analyzed by electrospray ionization tandem mass spectrometry (ESI-MS/MS) on a hybrid triple quadrupole time-of-flight apparatus (QSTAR®XL, Applied Biosystems) according to a standard laboratory procedure (Science and Technology of Milk and Eggs) described in Tarze et al. (2007).

By this analysis, the Inventors identified protein PF963, a secreted bacterial wall peptidase belonging to the NlpC/P60 family. The complete sequence of protein PF963 (SEQ ID NO 36; table I) can be deduced after determination of the complete sequence of the genome of strain CIP103027 by the Inventors.

III.2.2 Fusion of the N-Terminal Portion of Protein PF963 with the C-Terminal Portion of TRAIL The presence of a signal peptide at the N-terminal end of PF963 indicates that this enzyme is secreted via the Sec secretion pathway. The sequence of said signal peptide is SEQ ID NO 36. PCR primers were designed to amplify the DNA sequence corresponding to the promoter and to the signal peptide of protein PF963 (FIG. 3). Another pair of primers was designed to amplify the sequence of the human cytokine TRAIL. Only the active extracellular sequence Val$^{114}$-Gly$^{281}$ was amplified. The primer sequences are indicated in the following Table IV.

TABLE IV

| PCR primer | Sequence | Tm (° C.) | Total nucleotides | Nucleotides hybridizing with the matrix |
|---|---|---|---|---|
| P963Fw | ATACATATGCCACCGTGAG CTGCACCT (SEQ ID NO 38) | 70 | 27 | 18 |
| P963Rv | GCAAGCTTTCGGCCTGTGC AAGTGGTG (SEQ ID NO 39) | 71 | 27 | 19 |
| TRAILFw | GCAAGCTTAGTGAGAGAAA GAGGTCCTCAGAGAGTAG (SEQ ID NO 40) | 70 | 37 | 28 |
| TRAILRev | ACTGCAGTTAGCCAACTAA AAAGGCCCCGAAAAAACTG G (SEQ ID NO 41) | 70 | 39 | 32 |

The construction resulting from the fusion between 1) the promoter and the signal peptide of PF963 and 2) the Val$^{114}$-Gly$^{281}$ sequence of TRAIL was introduced in cloning vector pPK705 (Kiatpapan et al., 2000). The new pFB4:TRAIL expression plasmid is presented in FIG. 4.

III.2.3 Verification of the Genetic Construction

The sequence of the pFB4:TRAIL plasmid was verified (SEQ ID NO 42). The portion corresponding to the fusion protein ranges from nucleotides 8451 to 9070. This portion is translated in FIG. 5 (SEQ ID NO 43): the sequence corresponding to the PF963 peptide signal protein is underlined and the Val$^{114}$-Gly$^{281}$ sequence of TRAIL appears in bold.

The fusion protein has a sequence of 205 amino acid residues corresponding to a mass of 23,190 Da and an isoelectric point of 9.08. The elimination of the signal peptide leads to a sequence of 171 amino acid residues corresponding to a mass of 19,822 Da and an isoelectric point of 8.60.

Expression and secretion of the fusion protein were verified by Western blot using a commercial anti-TRAIL polyclonal antibody (Pab to TRAIL, Alexis Biochemicals). This antibody recognizes the monomeric form (31 kDa) as well as the dimeric form (63 kDa) of TRAIL in the Super-KillerTRAIL™ preparation (FIG. 6; lane 4). In the supernatant of the two clones of the transformed *P. freudenreichii* strain carrying the plasmid, a protein of 22 kDa, corresponding to the expected size, was detected by this antibody. This protein was absent in the supernatant of the wild strain.

IV-Development of a Second Recombinant *Propionibacterium* with the Goal of Inducing Both the Intrinsic and Extrinsic Apoptotic Pathways The inventors have optimized the plasmid pFB4: TRAIL by changing both the promoter region and the signal peptide to obtain the pCHH04: TRAIL plasmid, allowing secretion into the extracellular medium, of a higher amount of TRAIL into the supernatant.

IV.1 Materials and Methods

The construction of pCHH04:TRAIL is described in FIG. 7. The pFB4:TRAIL plasmid, which is a shuttle plasmid, was transformed into *Escherichia coli*. The propionibacterial insert containing the promoter PF963 and the signal peptide PS963 were excised using the appropriate restriction endonucleases. A new propionibacterial DNA fragment (set forth in SEQ ID NO: 69), containing the promoter region and the signal peptide of protein slpA of the *Propionibacterium freudenreichii* CIRM BIA 118 strain, was introduced in order to put the signal peptide in frame with the TRAIL coding sequence. The corresponding sequence was amplified by PCR (PSlpA_fwd_BamH1, which has the sequence set forth in SEQ ID NO: 70 and PS_SlpA-EcoRV-Rev_bis, which has the sequence set forth in SEQ ID NO: 71) from *Propionibacterium freudenreichii* genomic sequence, which was previously sequenced and annotated (Falentin et al., 2010a). This new plasmid, pCHH04:TRAIL, was then transformed into different strains of *Propionibacterium freudenreichii*. The corresponding supernatants were then analyzed by western blot with respect to TRAIL secretion as above described. Proteomic experiments, including gel electrophoresis and mass spectrometry, was conducted as previously described (Leverrier et al., 2004). TRAIL concentration was further quantified by Enzyme-Linked ImmunoSorbent Assay (ELISA) in supernatant of *Propionibacterium freudenreichii* transformed with pFB4:TRAIL or pCHH04: TRAIL plasmid according to the manufacturer's instructions (R&D System Europe, Lille, France). Human TRAIL standard concentration-response curves were used to quantify TRAIL levels in supernatants. TRAIL concentrations were determined using an automatic plate reader associated with genesis software (LabSystems Spectrophotometer, Cambridge, UK) and data were expressed in ng/ml.

IV.2 Results

In order to investigate secretion abilities in *Propionibacterium freudenreichii*, supernatants of several strains were analyzed by SDS-PAGE electrophoresis. FIG. 8 shows great variability, between strains, in terms of both number and amount of secreted proteins. In particular, *Propionibacterium freudenreichii* CIRM BIA 118 secreted elevated amounts of a 60 kDa protein identified by mass spectrometry as slpA. A translational fusion including slpA signal peptide and TRAIL C-terminal active extracellular part was then obtained (FIG. 7, pCHH04:TRAIL). This new construct was compared to pBF4:TRAIL in terms of TRAIL secretion in the CIRM BIA 118 strain. Western blot analysis of the corresponding culture supernatants revealed the presence of a 21 kDa polypeptide identified as TRAIL by immunoblotting. As shown in FIG. 9 (left panel), secretion into the extracellular medium of TRAIL was higher using the pCHH04:TRAIL construct, compared to pFB4:TRAIL. Furthermore, different strains of *Propionibacterium freudenreichii* were transformed using pCHH04:TRAIL and secreted TRAIL (FIG. 9, right panel). The amount of TRAIL secreted by *Propionibacterium freudenreichii* CIRM BIA 118 (pBF4:TRAIL) was 0.178 ng/ml while it was 22 ng/ml in *Propionibacterium freudenreichii* CIRM BIA 118 (pCHH04:TRAIL) (Table V). This evidences a 100-fold increase in secretion efficiency. Moreover, similar secretion efficiency was demonstrated in different strains of *Propionibacterium freudenreichii* (including CIRM BIA 512, 125, 118, 129 and 122 strains, FIG. 9 right panel and Table V).

TABLE V

ELISA quantification of human TRAIL in *Propionibacterium freudenreichii* supernatants (corresponding to supernatants analysed by western blot and shown in FIG. 9, left panel)

| ELISA | Human soluble TRAIL (ng/ml) |
|---|---|
| Cirm 118 WT | 0 |
| Cirm 118 pFB4:TRAIL | 0.178 |
| Cirm 118 pFB4 | 0 |
| Cirm 118 pCHH04:TRAIL | 22 |
| Cirm 122 pCHH04:TRAIL | Non Determined |
| Cirm 125 pCHH04:TRAIL | 24 |
| Cirm 129 pCHH04:TRAIL | 22 |
| Cirm 512 pCHH04:TRAIL | Non Determined |
| Cirm 118 pCHH04:TRAIL | 23 |

IV.3 Discussion

The expression and secretion construction pCHH04:TRAIL allows higher amounts of TRAIL secretion into the extracellular medium than the pFB4: TRAIL construction. The slpA promoter, isolated from strain CIRM BIA 118, is most probably stronger than PF963 promoter. The slpA signal peptide allows efficient secretion of the TRAIL human cytokine. Other slp proteins were then identified from the genomic sequence of several *Propionibacterium freudenreichii* strains. The corresponding signal peptides are presented in Table III and may also be used to allow heterologous protein expression in *Propionibacterium freudenreichii*.

V-Other Embodiments of the Invention

In the examples above, the Inventors made use of a *P. freudenreichii* signal peptide.

Advantageously, the present invention is implemented using one or more of the *P. freudenreichii* signal peptides listed in tables I to III above.

Of course, the present invention can be generalized to the use of any propionibacteria signal peptide. The means and methods described in detail above to obtain a recombinant vector enabling the expression and secretion into the extracellular medium of one or more amino acid sequences of interest (the $Val^{114}$-$Gly^{281}$ sequence of TRAIL in particular) are indeed suitable to the use of any propionibacteria signal peptide.

As an example, a recombinant vector in accordance with the present invention can be constructed using a signal peptide selected from the signal peptides of *Propionibacterium acnes*, whose genome is available in databases. Table II above gives examples of putative *P. acnes* signal peptide sequences.

One approach to identifying other signal peptides applicable to the present invention in particular involves aligning sequences in search of *Propionibacterium* sp. sequences homologous (for example, with roughly 80% homology, preferably at least 85%, 90%, 95% or roughly 98% homology) to signal peptides sequences of a *propionibacterium* used as a reference (such as *P. freudenreichii* or *P. acnes*), or searching for proteins secreted by a given *propionibacterium* and identifying possible corresponding signal peptides. Current computer software tools make it possible to easily identify putative signal peptide sequences within protein or genomic sequences (for example, the SignalP 3.0 software; Center for Biological Sequence Analysis, CBS; http://www.cbs.dtu.dk/services/SiqnalP/; Emanuelsson et al., 2007).

REFERENCES

Jan et al. 2002. Cell Death Differ. 9:179-188.
Falentin et al. 2010a. Plos One 5:e11748.
Falentin et al. 2010b. Int. J. Food Microbiol. 144:10-19.
Hervé et al. 2007. Int J Food Microbiol. 113:303-314.
Lan et al. 2007. Apoptosis 12:573-591.
Lan et al. 2007. Br J. Nutr. 97:714-724.
Lan et al. 2008. Br J. Nutr. 100:1251-1259.
Lacour et al. 2001. Cancer Res. 61:1645-1651.
Lacour et al. 2003. Oncogene 22:1807-1816.
Leverrier et al. 2004. Arch. Microbiol. 181:215-230.
Meurette et al. 2005. Clin. Cancer Res. 11:3075-3083.
Meurette et al. 2006. Ann N Y Acad. Sci. 1090:209-216.
Meurette et al. 2007. Cancer Res. 67:218-226.
Kiatpapan et al. 2000. Appl. Environ. Microbiol. 66:4688-4695.
Tarze et al. 2007. Oncogene 26:2606-2620.
Ganai et al. 2009. British Journal of Cancer. 101:1683-1691.
Hu et al. 2009. Cancer Gene Therapy. 16:655-663.
Patch J. A. and Barron A. E., 2002. Curr. Opin. Chem. Biol., 6(6):872-877. Review.
Ashkenazi A et al. 1999. J. Clin. Invest. 104:155-162.
Sträter J. et al. 2002. Gastroenterology 122:659-666.
Sambrook and Russell (2001) Molecular Cloning: A Laboratory Manual ($3^{rd}$ Ed.) Cold Spring Harbor Laboratory Press, Cold Spring Harbor, N.Y.
Emanuelsson et al. 2007. Nature Protocols 2:953-971.
Bougle et al. 1999. Scand. J. Gastroenterol. 34:144-148.
Zarate et al. 2000. J. Food Prot. 63:1214-1221.
Zhang et al. 2010. Cancer Gene Therapy 17:334-343
Lortal et al. 1993. Applied and Environmental Microbiology 59(8): 2369.

The invention claimed is:

1. A recombinant vector for expressing and secreting, by a *propionibacterium*, at least one eukaryotic peptide of interest or eukaryotic protein of interest, comprising at least:
   under the control of at least one suitable promoter,
   i) at least one nucleic acid sequence encoding a propionibacterial signal peptide, which is the sequence of the surface layer protein of a *P. freudenreichii* and,
   ii) at least one nucleic acid sequence encoding said eukaryotic peptide of interest or eukaryotic protein of interest;
   wherein said at least one nucleic acid sequence encoding a propionibacterial signal peptide is translationally fused to said at least one nucleic acid sequence encoding said eukaryotic peptide of interest or eukaryotic protein of interest,
   wherein said nucleic acid sequence encoding a propionibacterial signal peptide, which is the sequence of the surface layer protein of a *P. freudenreichii*, is selected from the group consisting of: the sequences SEQ ID NOs: 59 to 68.

2. The vector according to claim 1, wherein said eukaryotic peptide of interest or eukaryotic protein of interest has a biological activity selected from the group consisting of a proapoptotic activity, an anti-inflammatory activity and an immunomodulatory activity.

3. The vector according to claim 1, wherein said eukaryotic peptide of interest or eukaryotic protein of interest is selected from the group consisting of:
   a proapoptotic peptide or proapoptotic protein; and
   an anti-inflammatory peptide or anti-inflammatory protein.

4. The vector according to claim 1, wherein said eukaryotic peptide of interest or eukaryotic protein of interest is a cytokine.

5. The vector according to claim 1, wherein said eukaryotic peptide of interest or eukaryotic protein of interest is the proapoptotic TRAIL protein or the C-terminal extracellular domain of the TRAIL protein.

6. The vector according to claim 1, wherein said nucleic acid sequence encoding said eukaryotic peptide of interest or eukaryotic protein of interest is the sequence from amino acids 114 to 281 of the TRAIL protein sequence set forth in SEQ ID NO: 58.

7. The vector according to claim 1, wherein said at least one suitable promoter is the promoter of a gene encoding a surface layer protein of a *Propionibacterium freudenreichii*.

8. The vector according to claim 1, comprising the nucleotide sequence SEQ ID NO: 69 translationally fused to said nucleic acid sequence encoding said peptide of interest or eukaryotic protein of interest.

9. A recombinant *propionibacterium* comprising at least one vector according to claim 1.

10. The *propionibacterium* according to claim 9, which is a *Propionibacterium freudenreichii*.

11. A composition comprising an amount of at least one vector as defined in claim 1 and at least one pharmaceutically acceptable carrier.

12. The *propionibacterium* deposited on Jul. 23, 2009 under number I-4213 with the *Collection Nationale de Cultures de Microorganismes* (CNCM, Institut Pasteur, 25 rue du Docteur Roux, 75724 Paris Cedex 15, France).

13. The *propionibacterium* deposited on Nov. 13, 2012 under number CNCM I-4692 with the *Collection Nationale de Cultures de Microorganismes* (CNCM, Institut Pasteur, 25 rue du Docteur Roux, 75724 Paris Cedex 15, France).

14. A method for producing and secreting into the extracellular medium, by a *propionibacterium* as defined in any one of claims 9 to 13, at least one peptide of interest or eukaryotic protein of interest, wherein said method comprises at least:
   culturing said *propionibacterium* under suitable conditions; and
   recovering the culture medium containing said peptide of interest or eukaryotic protein of interest.

\* \* \* \* \*

UNITED STATES PATENT AND TRADEMARK OFFICE
CERTIFICATE OF CORRECTION

| | | |
|---|---|---|
| PATENT NO. | : 9,476,056 B2 | Page 1 of 1 |
| APPLICATION NO. | : 13/679344 | |
| DATED | : October 25, 2016 | |
| INVENTOR(S) | : Gwenael Jan et al. | |

It is certified that error appears in the above-identified patent and that said Letters Patent is hereby corrected as shown below:

On the Title Page

Correct item (71), Applicants, to read as follows:

--UNIVERSITÉ DE RENNES 1, Rennes (FR); INSTITUT NATIONAL DE LA SANTE ET DE LA RECHERCHE MEDICALE (INSERM), Paris (FR); INSTITUT NATIONAL DE LA RECHERCHE AGRONOMIQUE, Paris (FR)--.

Signed and Sealed this
Twenty-fifth Day of July, 2017

Joseph Matal
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 71

<210> SEQ ID NO 1
<211> LENGTH: 99
<212> TYPE: DNA
<213> ORGANISM: Propionibacterium freudenreichii

<400> SEQUENCE: 1

```
atgtcaaaga cactctctcg gatcgcatcc gtcgcttcgg ttgccgcgct cgccggcagc      60
atcaccgtca tcgccgggca gaacgcgtcc gccgacagc                            99
```

<210> SEQ ID NO 2
<211> LENGTH: 90
<212> TYPE: DNA
<213> ORGANISM: Propionibacterium freudenreichii

<400> SEQUENCE: 2

```
gtgaagaacg gtctcaagac cctgctcatt ggtggagtcg gcatcgcgac ccttgcggtc      60
ggcggcgtcg gaactgccat cgcagacaat                                      90
```

<210> SEQ ID NO 3
<211> LENGTH: 105
<212> TYPE: DNA
<213> ORGANISM: Propionibacterium freudenreichii

<400> SEQUENCE: 3

```
atgcgatcca ccacgacgaa ggcgtttgcc ggtgtcgctg tgctggcgct ggcgcttgct      60
ggctgcggct cgaattcggg ctcgtccacc aagtcggccg acagc                    105
```

<210> SEQ ID NO 4
<211> LENGTH: 93
<212> TYPE: DNA
<213> ORGANISM: Propionibacterium freudenreichii

<400> SEQUENCE: 4

```
atgctcactc gcaagagagt ggttgcagcg ggagctgccg ccaccctgtc cctcacggcg      60
tttgccgggt tgcagcccgc cagcgccgcc acc                                  93
```

<210> SEQ ID NO 5
<211> LENGTH: 108
<212> TYPE: DNA
<213> ORGANISM: Propionibacterium freudenreichii

<400> SEQUENCE: 5

```
atgggattca gggttggccg tcgtcccctc atcggggcag ttctcgccgg gtcgatggca      60
acactcgtgg gctgttccac ctcgggtagc ggcagtggag cctccagc                 108
```

<210> SEQ ID NO 6
<211> LENGTH: 111
<212> TYPE: DNA
<213> ORGANISM: Propionibacterium freudenreichii

<400> SEQUENCE: 6

```
atgcaggccc tccaaggaag gcgccggtca cgacgggtga tggcggccgc ggtagcagcc      60
ctcaccgcca tgaccgtgct gccctcccag ctcaacgccg ttgctgcacc c             111
```

<210> SEQ ID NO 7
<211> LENGTH: 90
<212> TYPE: DNA
<213> ORGANISM: Propionibacterium freudenreichii

```
<400> SEQUENCE: 7
atgtccactg gccgcatgaa gttcatcaag ctggcagttc ctgtcatcgt tgcctgctgc     60
ttgacgccaa tggctgcctt agctgatgtg                                      90

<210> SEQ ID NO 8
<211> LENGTH: 114
<212> TYPE: DNA
<213> ORGANISM: Propionibacterium freudenreichii

<400> SEQUENCE: 8
atggcgatga gggcacgtca cggcgtcgtc cggcttggtc tggtctgtct caccgcattg     60
gcggtcttcg gcacggcaaa tgtgtcgggt caggttgcgg tgatggctga gggc          114

<210> SEQ ID NO 9
<211> LENGTH: 108
<212> TYPE: DNA
<213> ORGANISM: Propionibacterium freudenreichii

<400> SEQUENCE: 9
ttgaaccagg ccctgtcgac gatgcgcctg aagatcggcg actccaccaa gcgcatccgg     60
atcttcttcg tcgtgatggc cgtggcgatc accctgctcg cgggacgg                 108

<210> SEQ ID NO 10
<211> LENGTH: 75
<212> TYPE: DNA
<213> ORGANISM: Propionibacterium freudenreichii

<400> SEQUENCE: 10
atgcgacgtc gcaccacgat tgcagccctc gctgctgtct tgagtttcag tccctggcc      60 gcccaggccg caccc                                                      75

<210> SEQ ID NO 11
<211> LENGTH: 132
<212> TYPE: DNA
<213> ORGANISM: Propionibacterium freudenreichii

<400> SEQUENCE: 11
atgcctagtc atgcggtgcg ggagacgcgg gcgaacaagt tgcgccggtt cctgcggccc     60
accgttgccc agggcgtgct cggtatcgcg ttctgcctcg tggccgccgt cggcgtggtg    120
cagatccgct cc                                                        132

<210> SEQ ID NO 12
<211> LENGTH: 111
<212> TYPE: DNA
<213> ORGANISM: Propionibacterium freudenreichii

<400> SEQUENCE: 12
atgtcacgga ttcaactccc ccggctgagc cggattgcga tcgcagcagc agcttccgct     60
gccctgatcg gcaccagctt catcgccccg gccacggcct tgccgcgcc g              111

<210> SEQ ID NO 13
<211> LENGTH: 75
<212> TYPE: DNA
<213> ORGANISM: Propionibacterium freudenreichii

<400> SEQUENCE: 13
ctagccgacc ttctcggcct tgctggccag gtcgtcgggg atcgtgaccc ccatcaggga     60
```

```
ggcggccttc tcatt                                                75
```

<210> SEQ ID NO 14
<211> LENGTH: 120
<212> TYPE: DNA
<213> ORGANISM: Propionibacterium freudenreichii

<400> SEQUENCE: 14

```
ttagttgttg gggacgagga gggagtggag ttcgatgacg tcgagggtgg gtgcggtggc    60
ggggcgggtg atggtttcgg tgccggtgtg tccttgggcg gtccaggtga tggtccaggt   120
```

<210> SEQ ID NO 15
<211> LENGTH: 60
<212> TYPE: DNA
<213> ORGANISM: Propionibacterium freudenreichii

<400> SEQUENCE: 15

```
tcagccagtt ggtgccggcc ttggcgtcgg cggcgtggga tacacgcgga actgggcgcc    60
```

<210> SEQ ID NO 16
<211> LENGTH: 114
<212> TYPE: DNA
<213> ORGANISM: Propionibacterium freudenreichii

<400> SEQUENCE: 16

```
atgttcattt cgcgcttccg tcgtgcggct gcggtcggcc tggccgccgt caccgcattg    60
tccgccactg cctgtagcgg ttcctcgtcg tcgtccagct catccgcgag ctcg         114
```

<210> SEQ ID NO 17
<211> LENGTH: 108
<212> TYPE: DNA
<213> ORGANISM: Propionibacterium freudenreichii

<400> SEQUENCE: 17

```
atgaagtccg cgacgcgacg cccgctgacg cgctggattg tcgccttcgg ggtggtgttg    60
gtgctggtca tcgccgggtc ggtggggctg catgcctccg gtgccctg              108
```

<210> SEQ ID NO 18
<211> LENGTH: 108
<212> TYPE: DNA
<213> ORGANISM: Propionibacterium freudenreichii

<400> SEQUENCE: 18

```
gtgaatccct tcgtcaagac ggcgcgcgtg gctatcacct cgacgctggt ggcaggctcg    60
ctcgccactg ccagcctcgt gtttgcacca cttgcacagg ccgattac              108
```

<210> SEQ ID NO 19
<211> LENGTH: 33
<212> TYPE: PRT
<213> ORGANISM: Propionibacterium freudenreichii

<400> SEQUENCE: 19

```
Met Ser Lys Thr Leu Ser Arg Ile Ala Ser Val Ala Ser Val Ala Ala
1               5                  10                  15

Leu Ala Gly Ser Ile Thr Val Ile Ala Gly Gln Asn Ala Ser Ala Asp
            20                  25                  30

Ser
```

<210> SEQ ID NO 20
<211> LENGTH: 30

<212> TYPE: PRT
<213> ORGANISM: Propionibacterium freudenreichii

<400> SEQUENCE: 20

```
Met Lys Asn Gly Leu Lys Thr Leu Leu Ile Gly Gly Val Gly Ile Ala
1               5                   10                  15
Thr Leu Ala Val Gly Gly Val Gly Thr Ala Ile Ala Asp Asn
            20                  25                  30
```

<210> SEQ ID NO 21
<211> LENGTH: 35
<212> TYPE: PRT
<213> ORGANISM: Propionibacterium freudenreichii

<400> SEQUENCE: 21

```
Met Arg Ser Thr Thr Thr Lys Ala Phe Ala Gly Val Ala Val Leu Ala
1               5                   10                  15
Leu Ala Leu Ala Gly Cys Gly Ser Asn Ser Gly Ser Ser Thr Lys Ser
            20                  25                  30
Ala Asp Ser
        35
```

<210> SEQ ID NO 22
<211> LENGTH: 31
<212> TYPE: PRT
<213> ORGANISM: Propionibacterium freudenreichii

<400> SEQUENCE: 22

```
Met Leu Thr Arg Lys Arg Val Val Ala Ala Gly Ala Ala Ala Thr Leu
1               5                   10                  15
Ser Leu Thr Ala Phe Ala Gly Leu Gln Pro Ala Ser Ala Ala Thr
            20                  25                  30
```

<210> SEQ ID NO 23
<211> LENGTH: 36
<212> TYPE: PRT
<213> ORGANISM: Propionibacterium freudenreichii

<400> SEQUENCE: 23

```
Met Gly Phe Arg Val Gly Arg Arg Pro Leu Ile Gly Ala Val Leu Ala
1               5                   10                  15
Gly Ser Met Ala Thr Leu Val Gly Cys Ser Thr Ser Gly Ser Gly Ser
            20                  25                  30
Gly Ala Ser Ser
        35
```

<210> SEQ ID NO 24
<211> LENGTH: 37
<212> TYPE: PRT
<213> ORGANISM: Propionibacterium freudenreichii

<400> SEQUENCE: 24

```
Met Gln Ala Leu Gln Gly Arg Arg Arg Ser Arg Arg Val Met Ala Ala
1               5                   10                  15
Ala Val Ala Ala Leu Thr Ala Met Thr Val Leu Pro Ser Gln Leu Asn
            20                  25                  30
Ala Val Ala Ala Pro
        35
```

<210> SEQ ID NO 25
<211> LENGTH: 30

<212> TYPE: PRT
<213> ORGANISM: Propionibacterium freudenreichii

<400> SEQUENCE: 25

Met Ser Thr Gly Arg Met Lys Phe Ile Lys Leu Ala Val Pro Val Ile
1               5                   10                  15

Val Ala Cys Cys Leu Thr Pro Met Ala Ala Leu Ala Asp Val
            20                  25                  30

<210> SEQ ID NO 26
<211> LENGTH: 38
<212> TYPE: PRT
<213> ORGANISM: Propionibacterium freudenreichii

<400> SEQUENCE: 26

Met Ala Met Arg Ala Arg His Gly Val Val Arg Leu Gly Leu Val Cys
1               5                   10                  15

Leu Thr Ala Leu Ala Val Phe Gly Thr Ala Asn Val Ser Gly Gln Val
            20                  25                  30

Ala Val Met Ala Glu Gly
        35

<210> SEQ ID NO 27
<211> LENGTH: 36
<212> TYPE: PRT
<213> ORGANISM: Propionibacterium freudenreichii

<400> SEQUENCE: 27

Met Asn Gln Ala Leu Ser Thr Met Arg Leu Lys Ile Gly Asp Ser Thr
1               5                   10                  15

Lys Arg Ile Arg Ile Phe Phe Val Val Met Ala Val Ala Ile Thr Leu
            20                  25                  30

Leu Ala Gly Arg
        35

<210> SEQ ID NO 28
<211> LENGTH: 25
<212> TYPE: PRT
<213> ORGANISM: Propionibacterium freudenreichii

<400> SEQUENCE: 28

Met Arg Arg Arg Thr Thr Ile Ala Ala Leu Ala Ala Val Leu Ser Phe
1               5                   10                  15

Ser Pro Leu Ala Ala Gln Ala Ala Pro
            20                  25

<210> SEQ ID NO 29
<211> LENGTH: 44
<212> TYPE: PRT
<213> ORGANISM: Propionibacterium freudenreichii

<400> SEQUENCE: 29

Met Pro Ser His Ala Val Arg Glu Thr Arg Ala Asn Lys Leu Arg Arg
1               5                   10                  15

Phe Leu Arg Pro Thr Val Ala Gln Gly Val Leu Gly Ile Ala Phe Cys
            20                  25                  30

Leu Val Ala Ala Val Gly Val Val Gln Ile Arg Ser
        35                  40

<210> SEQ ID NO 30
<211> LENGTH: 37

<212> TYPE: PRT
<213> ORGANISM: Propionibacterium freudenreichii

<400> SEQUENCE: 30

Met Ser Arg Ile Gln Leu Pro Arg Leu Ser Arg Ile Ala Ile Ala Ala
1               5                   10                  15

Ala Ala Ser Ala Ala Leu Ile Gly Thr Ser Phe Ile Ala Pro Ala Thr
                20                  25                  30

Ala Phe Ala Ala Pro
                35

<210> SEQ ID NO 31
<211> LENGTH: 25
<212> TYPE: PRT
<213> ORGANISM: Propionibacterium freudenreichii

<400> SEQUENCE: 31

Met Lys Arg Arg Thr Leu Leu Gly Thr Leu Gly Ile Met Gly Leu Ser
1               5                   10                  15

Val Pro Leu Ala Ala Cys Ser Ser Lys
                20                  25

<210> SEQ ID NO 32
<211> LENGTH: 40
<212> TYPE: PRT
<213> ORGANISM: Propionibacterium freudenreichii

<400> SEQUENCE: 32

Met Val Thr Gly Gly Asn Asp Met Pro Ser Lys Arg Ile Thr Thr Trp
1               5                   10                  15

Pro Gly Ile Ser Ala Leu Ser Ala Leu Ile Ala Gly Met Leu Leu Ala
                20                  25                  30

Pro Leu Pro Val Ala Ala Asp Gly
                35                  40

<210> SEQ ID NO 33
<211> LENGTH: 20
<212> TYPE: PRT
<213> ORGANISM: Propionibacterium freudenreichii

<400> SEQUENCE: 33

Met Ala Met Val Met Ala Ser Leu Ala Met Phe Gly Ala Ser Arg Ala
1               5                   10                  15

Ser Ala Ala Asp
                20

<210> SEQ ID NO 34
<211> LENGTH: 38
<212> TYPE: PRT
<213> ORGANISM: Propionibacterium freudenreichii

<400> SEQUENCE: 34

Met Phe Ile Ser Arg Phe Arg Arg Ala Ala Ala Val Gly Leu Ala Ala
1               5                   10                  15

Val Thr Ala Leu Ser Ala Thr Ala Cys Ser Gly Ser Ser Ser Ser Ser
                20                  25                  30

Ser Ser Ser Ala Ser Ser
                35

<210> SEQ ID NO 35
<211> LENGTH: 36

<210> SEQ ID NO 35
<211> LENGTH: 35 (implied)
<212> TYPE: PRT
<213> ORGANISM: Propionibacterium freudenreichii

<400> SEQUENCE: 35

```
Met Lys Ser Ala Thr Arg Arg Pro Leu Thr Arg Trp Ile Val Ala Phe
1               5                   10                  15
Gly Val Val Leu Val Leu Val Ile Ala Gly Ser Val Gly Leu His Ala
                20                  25                  30
Ser Gly Ala Leu
            35
```

<210> SEQ ID NO 36
<211> LENGTH: 36
<212> TYPE: PRT
<213> ORGANISM: Propionibacterium freudenreichii

<400> SEQUENCE: 36

```
Met Asn Pro Phe Val Lys Thr Ala Arg Val Ala Ile Thr Ser Thr Leu
1               5                   10                  15
Val Ala Gly Ser Leu Ala Thr Ala Ser Leu Val Phe Ala Pro Leu Ala
                20                  25                  30
Gln Ala Asp Tyr
            35
```

<210> SEQ ID NO 37
<211> LENGTH: 572
<212> TYPE: PRT
<213> ORGANISM: Propionibacterium freudenreichii

<400> SEQUENCE: 37

```
Met Asn Pro Phe Val Lys Thr Ala Arg Val Ala Ile Thr Ser Thr Leu
1               5                   10                  15
Val Ala Gly Ser Leu Ala Thr Ala Ser Leu Val Phe Ala Pro Leu Ala
                20                  25                  30
Gln Ala Asp Tyr Ser Pro Leu Ala Ala Thr Ala Thr Val Asn Val Arg
            35                  40                  45
Gln Gly Pro Asp Thr Ser Ser Ser Val Leu Ala Thr Leu Ser Ser Gly
    50                  55                  60
Asp Thr Val Thr Gln Arg Gly Ala Glu Gln Asp Gly Trp Leu Pro Ile
65                  70                  75                  80
Thr Tyr Asn Gly Ala Asn Ala Trp Ile Gln Ala Gln Tyr Val Ala Ser
                85                  90                  95
Thr Thr Ala Ala Thr Gln Lys Asp Gln Ile Ser Thr Ala Glu Leu Thr
            100                 105                 110
Ala Asp Ala Tyr Val Arg Thr Ala Ala Asn Ala Asn Ala Trp Val Leu
        115                 120                 125
Gly Thr Ala His Thr Gly Asp Lys Val Gly Ile Thr Gly Gln Ala Ser
    130                 135                 140
Gly Asp Tyr Thr Pro Val Asn Phe Tyr Gly Arg Ala Gly Trp Ile Ala
145                 150                 155                 160
Thr Lys Leu Leu Ser Ala Ala Asp Ala Ser Val Thr Ser Ile Lys Ile
                165                 170                 175
Thr Thr Ala Ile Ser Ser Asp Tyr Leu Trp Val Arg Gly Gly Glu Ser
            180                 185                 190
Thr Ala Ala Gln Ser Ile Gly Met Leu Tyr Pro Gly Asp Arg Val Asp
        195                 200                 205
Val Thr Gly Asp Pro Val Gly Gly Trp Val Pro Ile Asn Phe Asn Gly
```

```
            210                 215                 220
Lys Thr Ala Phe Val Ala Ala Asn Tyr Ser Arg Tyr Leu Thr Asp Pro
225                 230                 235                 240

Thr Val Val Thr Leu Ser Thr Lys Thr Asp Val Thr Asn Lys Asp Thr
                245                 250                 255

Ala Thr Ser Thr Gly Thr Asp Ser Ser Thr Ala Gly Gly Ser Thr Ala
            260                 265                 270

Thr Thr Pro Thr Thr Thr Ala Pro Thr Thr Ala Pro Ala Thr Lys
        275                 280                 285

Pro Thr Thr Thr Pro Pro Ala Thr Thr Gln Ala Ala Ser Thr Lys
    290                 295                 300

Tyr Thr Thr Ala Asp Val Asn Val Arg Val Gly Pro Gly Ile Asp Gln
305                 310                 315                 320

Gln Pro Val Thr Val Leu Lys Glu Asn Ser Gln Val Ala Ala Thr Gly
                325                 330                 335

Lys Thr Ser Gly Asp Trp Thr Glu Val Ser Tyr Asp Gly Ala Ser Arg
            340                 345                 350

Trp Ile Ser Ser Gln Tyr Leu Ser Asp Thr Lys Gln Ala Glu Ala Pro
        355                 360                 365

Ala Pro Ala Pro Ala Pro Asp Pro Thr Pro Ala Gly Pro Thr Gly Ser
    370                 375                 380

Arg Trp Thr Thr Ala Ala Leu Asn Ala Tyr Gly Ser Ser Thr Gln Pro
385                 390                 395                 400

Lys Pro Ala Thr Val Val Pro Glu Gly Thr Gln Val Glu Leu Thr
                405                 410                 415

Gly Lys Gln Ala Asp Gly Arg Ser Glu Tyr Thr Trp Asn Gly Thr Thr
            420                 425                 430

Tyr Trp Ser Ala Thr Glu Tyr Leu Gly Thr Asn Ala Pro Ala Thr Asn
        435                 440                 445

Thr Ser Ala Asn Thr Ala Lys Pro Gly Ala Asn Ala Val Glu Thr Ala
    450                 455                 460

Ile Asn Phe Ala Met Ser Lys Leu Gly Pro Tyr Val Trp Gly Gly
465                 470                 475                 480

Thr Gly Pro Val Gly Tyr Asp Cys Ser Gly Leu Met Gln Ala Tyr
                485                 490                 495

Ala Ala Ala Gly Val Thr Leu Pro Arg Val Thr Trp Asp Gln Val Asn
            500                 505                 510

Ala Gly Lys Gln Val Ser Val Gly Asp Leu Gln Pro Gly Asp Leu Val
        515                 520                 525

Phe Phe Tyr Asp Asn Gly His Val Gly Met Tyr Ile Gly Asn Gly Asn
    530                 535                 540

Ile Val Asn Ala Leu Asn Glu Asp Ala Gly Ile Val Val Thr Pro Ile
545                 550                 555                 560

Ser Tyr Met Pro Ile Ser Ala Ala Val Arg Ile Ala
                565                 570
```

<210> SEQ ID NO 38
<211> LENGTH: 27
<212> TYPE: DNA
<213> ORGANISM: Artificial Sequence
<220> FEATURE:
<223> OTHER INFORMATION: Synthetic primer P963Fw

<400> SEQUENCE: 38
atacatatgc caccgtgagc tgcacct         27

<210> SEQ ID NO 39
<211> LENGTH: 27
<212> TYPE: DNA
<213> ORGANISM: Artificial Sequence
<220> FEATURE:
<223> OTHER INFORMATION: Synthetic primer P963Rv

<400> SEQUENCE: 39
gcaagctttc ggcctgtgca agtggtg                                27

<210> SEQ ID NO 40
<211> LENGTH: 37
<212> TYPE: DNA
<213> ORGANISM: Artificial Sequence
<220> FEATURE:
<223> OTHER INFORMATION: Synthetic primer TRAILFw

<400> SEQUENCE: 40
gcaagcttag tgagagaaag aggtcctcag agagtag                     37

<210> SEQ ID NO 41
<211> LENGTH: 39
<212> TYPE: DNA
<213> ORGANISM: Artificial Sequence
<220> FEATURE:
<223> OTHER INFORMATION: Synthetic primer TRAILRv

<400> SEQUENCE: 41
actgcagtta gccaactaaa aaggccccga aaaaactgg                   39

<210> SEQ ID NO 42
<211> LENGTH: 9073
<212> TYPE: DNA
<213> ORGANISM: Artificial Sequence
<220> FEATURE:
<223> OTHER INFORMATION: Sequence of the plasmid pFB4:TRAIL

<400> SEQUENCE: 42
ggtcgactct agagggatcc ggcggaactt cacgtcctgg cggtggagtt ggcgggcgcg      60
ttccagccgt tcctccagca cggtgatccg ggcctccaga cgctcacgct cacctgctc     120 caggtgccgg gtcaccgtca ccgtccgcac cggccgggcc tcggcctggg cggcccggcg    180
ttcctcactg gcccgcttcc ggcaatcgtc ggaacaccac accgggggcc gaccccgccc    240
accgtgggcc tccaccggcg ccccgcagtg gggacacgcc cgcagcgccg acgcatcctc    300
atccaaggcc atcaccgggt cggaatccat acccgaaacc atatcgtccg acgatgaac    360 tgcgccagac agctaagaat gcacgaggtg tgtctccgat tctcaggaaa cgctcagcat    420
tttccgagac gttcggcgca cgcacacacc cccacaagaa ccgacccgcc cagcatccgc    480
cgacacgtcg atccgcaccc gcgatgggct ggccgaggcc gactacgacc gctagtcagc    540
acctgcgctg atctaccgtc gccctgaccg actctcccgt cgggattgtc gccggccgct    600
gccagcatgg acctgcggcc ccgcccctc gccctgcaac tcgagggagg cggggccgtc    660
caccccccac accaccccga caccgtgatg cgcccatgtc gcctaacggg ttgcccgacc    720
tccccgacat caagaaaacc tgacaccgtc gccgcaagcg ctacactgac tactagtagt    780
caggaggtgc gtgatgacca tcgccacatc ggtgaaactc tccgaagaga ccggccgcaa    840
actcgatgaa ctagcccggg ccaccggggcg atccaagtcc tactacctgc gcaggccat    900 cgaggaccac atcgaccaga tggtccacga ctacgccatc gcccgactcg ccgacgacgt    960

```
gcgagccggc cgggccgcca cctacagcgc cgacgaagtg gaccagatcc ttggcctgga   1020
cgattgagta caccgacccc gccgtcaaag cactgcgcaa actcgaccga gcccaggccc   1080
gccgcatcac cgcctacata cgtgagctca ccggcctgga cgatcccac caacgcggga    1140 aaggaaaata aaaaggggga cctctagggt ccccaattaa ttagtaatat aatctattaa   1200
aggtcattca aaaggtcatc caccggatca attcccctgc tcgcgcaggc tgggtgccaa   1260
gctctcgggt aacatcaagg cccgatcctt ggagcccttg ccctcccgca cgatgatcgt   1320
gccgtgatcg aaatccagat ccttgacccg cagttgcaaa ccctcactga tccgtaatgt   1380
gagttagctc actcattagg cacccccaggc tttacactt atgcttccgg ctcgtatgtt    1440
gtgtggaatt gtgagcggat aacaatttca cacaggaaac agctatgacc atgattacgc   1500
caagctgtgg cgtacaccgt cgcctcggtc ggcccgtaga gattggcgat cccgaccgca   1560
gcaccaccga gaacgtcccc gacgtggccg accagcccgt catcgtcaac gcctgaccgc   1620
ggtgcggaca gccgtgtcg cgaccggccg tgcggaatta agccggcccg taccctgtga    1680
atagaggtcc gctgtgacac aagaatccct gttacttctc gaccgtattg attcggatga   1740
ttcctacgcg agcctgcgga acgaccagga attctgggag ccgctggccc gccgagccct   1800
ggaggagctc ggctgccgg tgccgccggt gctgcgggtg cccggcgaga gcaccaaccc    1860
cgtactggtc ggcgagcccg acccggtgat caagctgttc ggcgagcact ggtgcggtcc   1920
ggagagcctc gcgtcggagt cggaggcgta cgcggtcctg gcggacgccc cggtgccggt   1980
gccccgcctc ctcggccgcg gcgagctgcg gcccggcacc ggagcctggc cgtggcccta   2040
cctggtgatg agccggatga ccggcaccac ctggcggtcc gcgatggacg gcacgaccga   2100
ccggaacgcg ctgctcgccc tggcccgcga actcggccgg gtgctcggcc ggctgcacag   2160
ggtgccgctg accgggaaca ccgtgctcac ccccattcc gaggtcttcc cggaactgct    2220
gcgggaacgc gcgcggcga ccgtcgagga ccaccgcggg tggggctacc tctcgccccg    2280
gctgctggac cgcctggagg actggctgcc ggacgtggac acgctgctgg ccggccgcga   2340
accccggttc gtccacggcg acctgcacgg gaccaacatc ttcgtggacc tggccgcgac   2400
cgaggtcacc gggatcgtcg acttcaccga cgtctatgcg ggagactccc gctacagcct   2460
ggtgcaactg catctcaacg ccttccgggg cgaccgcgag atcctggccg cgctgctcga   2520
cggggcgcag tggaagcgga ccgaggactt cgcccgcgaa ctgctcgcct tcaccttcct   2580
gcacgacttc gaggtgttcg aggagacccc gctggatctc tccggcttca ccgatccgga   2640
ggaactggcg cagttcctct gggggccgcc ggacaccgcc ccggcgcct gacgccccgg    2700 gcctaccgct gacacgcaac cccgcaccct cggccaagac gtcacacacc accgccccca   2760
ccgagcactg aggatgtcaa ctcgcccgag ccggcctgcc ggccgtctta cgggttgtct   2820
tggcgggcgg ggtgtctttg ccctggccca gcagcccac gatctcccgc agcgtgtcgg    2880
cggtggcggc gtcccgggcc gcctgacgct ccgcctccgc cctggcctgc tcggctgcct   2940
gcgcccgatc ctccgcggcg gcggcctgct ccctcgcctc ggccagctcg ccggtcaggg   3000
cctcgacccg ggcctgcacc tgccccaggc gcgcctccgc ctcctgctgc acctgctcgg   3060
cccgggcctc cgcctggtcc cgggccgcct cggcctcggc cggtgctga tccgccaggg    3120 ccgcctcggc caccgcttcg gcctgcccat ccaccgcctg ctcggcccga gccccgaact   3180
cctcgcgggc cgcatcactc gcctgacgcc acgccgccgc ccacaccaga cccaacggct   3240
ccgacagatc cggcggggcc ggcgtctgga ccgacgccga gacgtcgcgc aggaaccccg   3300
ccgcagcgtc ggtggagcac cccgcctccg ccttcaacga ccgcaccgtc acccgccgac   3360
```

```
ccgcaccgct caaccgcgca taggccgccg ccaaccttga cccattcgac tccatgaccc    3420
accctcccat tctgtaccct gtacctgttc ctaggtacgt tcctaatgta cctcaccgga    3480
tgcagaaccc gcaaccccc  tcacactccc cctgcacggg gcccgccccc tgcaccccg     3540 ctgccgcgcc cgctcctgcg tcgcggcctt gcccctgccc aacgccgggc cggcgggcag    3600
cccaccagag gctctgtgag acgtcggcgc cccgtccac  ctaccctaaa gaccaaccgg    3660
ccgtggaaac gtctgtgagg agccttgtag gagttcccag gacaagccag caaggccggg    3720
cctgacggcc cggaaaggaa gtcgctgcgc tcctacgaag aagcccctct ggggaccccc    3780
agaccccgga actatctgat ttggtttagc ggcgtacttc cgtcataccg gaatttatgg    3840
catgctgtgg tcatggcgac gacgacggtc gatgagcagt gggagcaggt gtggctgccc    3900
cgctggcccc tggcctccga cgacctggca gcgggcatct accggatggc ccgcccctcg    3960
gcgctggggg tccgatacat cgaggtcaac ccccaagcca tcagcaacct cctcgtggtc    4020
gactgcgacc accccgacgc tgccatgcgc gccgtctggg accgcacga  ctggctgccc    4080 aacgccatcg tcgagaaccc cgacaacggc cacgcccacg ccgtgtgggc cctggaagca    4140
gccatcccgc gcaccgagta cgcccaccgc aagcccatcg cctacgccgc cgccgtcacc    4200
gagggcctgc gccgatccgt cgacggagac gcctcctacg ccggcctgat caccaagaac    4260
cccgaacacc ccgcctggaa caccacctgg tgcaccgacc acctctaccg gctggccgag    4320
ctcgacaccc acctggatgc cgccggcctc atgcccgccc cctcctggcg acgcacccgc    4380
cggcgcaacc ccgtcggcct gggccgcaac tgcgccatct tcgagaccgc ccgcacctgg    4440
gcctaccgcg acgcccgccg catccgacaa cgccacgaat acccgaccgc cgaggactcg    4500
gccgacctgc acgccgtcat cgcctccacc gtcgaggcgc tcaacgccgg ctacagcgaa    4560
cccctgccgg cccgcgaggc cgccggcatc gccgccagca tccaccgatg gatcacccac    4620
cgtttctacg gctggatcga ctcccacacc gtcaacgagg ccactttctc caccatccag    4680
agctacagag gacacaaggg agccggcaag gctcgtcctc gtgcccgccg tgctgcttct    4740
atcaccgatt gggaggcatg atggctgacg tccagcaccg cgtgaagcgt cggggcacgg    4800
cccgcgaggc cgcagaacgt gtaggggcct ccatccgaac cgcccagcgg tggacctcca    4860
tcccccgtga ggaatggatc actcagaagg ccgtcgagcg tgaggagatc cgggcctaca    4920
agtacgacga ggggcacacg tggggcgaga cctcgcgcca cttcgggatc gcgaagacca    4980
ccgcccagga gcgggcccgg cgggctcgaa gggagcgggc ggccgaagcg gagaaggctg    5040
ccgaggaggc cgaggccgcg ctgcgtccga cactcttcga gggccaggag caaggttctg    5100
catgagcaac cccgagtcct cgggtagacc gtctggcccg acgttaagca tggctgaagc    5160
ggcccgtgcc tgtgggggtt cagtgtccac ggtgaggcgt caccgtgatg ccctggtggc    5220
ccacggtgct acccgtcatg acgcgtcatg ggtgataccc ctatcagcgt tgatttcatg    5280
cggtttgatg cccggggtga cacccctga  tgccccgtca cccaataacg tggcgcctgc    5340
catgacgtcc cacggtgacg cccccctgac ggggaagtc  caagagctgc gcgagcgact    5400
ggccaacgct gagcatcgag ccgagctagc agtagaggtt ggggacgacg tctcggcgac    5460
tccggagaac accaagtcag ggtctcatga gtgtgcgata gcttgagctg tctaccaatc    5520
tggatatagc tatatcggtc gtttgtgtct gattcgccag tgagccaacg gcggggggcga   5580 cacgcggtgg cgaaaccccc tggcagaatt cgtaatcatg gtcatagctg tttcctgtgt    5640
gaaattgtta tccgctcaca attccacaca acatacgagc cggaagcata aagtgtaaag    5700
```

-continued

```
cctgggtgc ctaatgagtg agctaactca cattaattgc gttgcgctca ctgcccgctt    5760
tccagtcggg aaacctgtcg tgccagctgc attaatgaat cggccaacgc gcggggagag    5820
gcggtttgcg tattgggcgc tcttccgctt cctcgctcac tgactcgctg cgctcggtcg    5880
ttcggctgcg gcgagcggta tcagctcact caaaggcggt aatacggtta ccacagaat    5940 caggggataa cgcaggaaag aacatgtgag caaaaggcca gcaaaaggcc aggaaccgta    6000
aaaaggccgc gttgctggcg tttttccata ggctccgccc ccctgacgag catcacaaaa    6060
atcgacgctc aagtcagagg tggcgaaacc cgacaggact ataaagatac caggcgtttc    6120
cccctggaag ctccctcgtg cgctctcctg ttccgaccct gccgcttacc ggatacctgt    6180
ccgcctttct cccttcggga agcgtggcgc tttctcatag ctcacgctgt aggtatctca    6240
gttcggtgta ggtcgttcgc tccaagctgg gctgtgtgca cgaaccccc gttcagcccg    6300 accgctgcgc cttatccggt aactatcgtc ttgagtccaa cccggtaaga cacgacttat    6360
cgccactggc agcagccact ggtaacagga ttagcagagc gaggtatgta ggcggtgcta    6420
cagagttctt gaagtggtgg cctaactacg gctacactag aaggacagta tttggtatct    6480
gcgctctgct gaagccagtt accttcggaa aaagagttgg tagctcttga tccggcaaac    6540
aaaccaccgc tggtagcggt ggtttttttg tttgcaagca gcagattacg cgcagaaaaa    6600
aaggatctca agaagatcct ttgatctttt ctacggggtc tgacgctcag tggaacgaaa    6660
actcacgtta agggattttg gtcatgagat tatcaaaaag gatcttcacc tagatccttt    6720
taaattaaaa atgaagtttt aaatcaatct aaagtatata tgagtaaact tggtctgaca    6780
gttaccaatg cttaatcagt gaggcaccta tctcagcgat ctgtctattt cgttcatcca    6840
tagttgcctg actccccgtc gtgtagataa ctacgatacg ggagggctta ccatctggcc    6900
ccagtgctgc aatgataccg cgagacccac gctcaccggc tccagattta tcagcaataa    6960
accagccagc cggaagggcc gagcgcagaa gtggtcctgc aactttatcc gcctccatcc    7020
agtctattaa ttgttgccgg gaagctagag taagtagttc gccagttaat agtttgcgca    7080
acgttgttgc cattgctaca ggcatcgtgg tgtcacgctc gtcgtttggt atggcttcat    7140
tcagctccgt ttcccaacga tcaaggcgag ttacatgatc ccccatgttg tgcaaaaaag    7200
cggttagctc cttcggtcct ccgatcgttg tcagaagtaa gttggccgca gtgttatcac    7260
tcatggttat ggcagcactg cataattctc ttactgtcat gccatccgta agatgctttt    7320
ctgtgactgg tgagtactca accaagtcat tctgagaata gtgtatgcgg cgaccgagtt    7380
gctcttgccc ggcgtcaata cgggataata ccgcgccaca tagcagaact ttaaaagtgc    7440
tcatcattgg aaaacgttct cggggcgaa aactctcaag gatcttaccg ctgttgagat    7500
ccagttcgat gtaacccact cgtgcaccca actgatcttc agcatctttt actttcacca    7560
gcgtttctgg gtgagcaaaa acaggaaggc aaaatgccgc aaaaaaggga ataagggcga    7620
cacggaaatg ttgaatactc atactcttcc tttttcaata ttattgaagc atttatcagg    7680
gttattgtct catgagcgga tacatatttg aatgtatttta gaaaaataaa caaatagggg    7740
ttccgcgcac atttccccga aaagtgccac ctgacgtcta agaaaccatt attatcatga    7800
cattaaccta taaaaatagg cgtatcacga ggccctttcg tctcgcgcgt ttcggtgatg    7860
acggtgaaaa cctctgacac atgcagctcc cggagacggt cacagcttgt ctgtaagcgg    7920
atgccgggag cagacaagcc cgtcaggcg cgtcagcggg tgttggcggg tgtcggggct    7980
ggcttaacta tgcggcatca gagcagattg tactgagagt gcaccatatg ccaccgtgag    8040
ctgcacctga atcagctgag aatgccctga accctcaaac ccgcaccctg aacctcaacc    8100
```

```
ttgcgttgaa cccgagggt gcgggttgga cgcgcacccc gaccactgca ccccgcgggg    8160 cgccctgtg acgaccatgg tctgattcac gcctgaaatc actccccgcc ggggtggaga    8220
accacgtcaa cgcggccgtg gatcacatcg ggcgtcgaaa acaaccccc catttcccca    8280 accctcaacc tgatcctgca ctgttgtcgg gtttgctgag agccgcctaa gctgccgcac    8340
gttgtcccag ttggggcgtg gcctgctgca tacggggccg ggaaagacgc ctcacctggg    8400
atgacgcgga ccattggaca cggccttttcc ggccgcggga aggaccagac gtgaatccct    8460
tcgtcaagac ggcgcgcgtg gctatcacct cgacgctggt ggcaggctcg ctcgccactg    8520
ccagcctcgt gtttgcacca cttgcacagg ccgaaagctt agtgagagaa agaggtcctc    8580
agagagtagc agctcacata actgggacca gaggaagaag caacacattg tcttctccaa    8640
actccaagaa tgaaaaggct ctgggccgca aaataaactc ctgggaatca tcaaggagtg    8700
ggcattcatt cctgagcaac ttgcacttga ggaatggtga actggtcatc catgaaaaag    8760
ggttttacta catctattcc caaacatact ttcgatttca ggaggaaata aagaaaaca    8820 caaagaacga caaacaaatg gtccaatata tttacaaata cacaagttat cctgacccta    8880
tattgttgat gaaaagtgct agaaatagtt gttggtctaa agatgcagaa tatggactct    8940
attccatcta tcaaggggga atatttgagc ttaaggaaaa tgacagaatt tttgtttctg    9000
taacaaatga gcacttgata gacatggacc atgaagccag ttttttcggg gccttttag     9060 ttggctaact gca                                                      9073
```

<210> SEQ ID NO 43
<211> LENGTH: 205
<212> TYPE: PRT
<213> ORGANISM: Artificial Sequence
<220> FEATURE:
<223> OTHER INFORMATION: Fusion protein sequence encoded by pFB4:TRAIL

<400> SEQUENCE: 43

```
Met Asn Pro Phe Val Lys Thr Ala Arg Val Ala Ile Thr Ser Thr Leu
1               5                   10                  15

Val Ala Gly Ser Leu Ala Thr Ala Ser Leu Val Phe Ala Pro Leu Ala
            20                  25                  30

Gln Ala Glu Ser Leu Val Arg Glu Arg Gly Pro Gln Arg Val Ala Ala
        35                  40                  45

His Ile Thr Gly Thr Arg Gly Arg Ser Asn Thr Leu Ser Ser Pro Asn
    50                  55                  60

Ser Lys Asn Glu Lys Ala Leu Gly Arg Lys Ile Asn Ser Trp Glu Ser
65                  70                  75                  80

Ser Arg Ser Gly His Ser Phe Leu Ser Asn Leu His Leu Arg Asn Gly
                85                  90                  95

Glu Leu Val Ile His Glu Lys Gly Phe Tyr Tyr Ile Tyr Ser Gln Thr
            100                 105                 110

Tyr Phe Arg Phe Gln Glu Glu Ile Lys Glu Asn Thr Lys Asn Asp Lys
        115                 120                 125

Gln Met Val Gln Tyr Ile Tyr Lys Tyr Thr Ser Tyr Pro Asp Pro Ile
    130                 135                 140

Leu Leu Met Lys Ser Ala Arg Asn Ser Cys Trp Ser Lys Asp Ala Glu
145                 150                 155                 160

Tyr Gly Leu Tyr Ser Ile Tyr Gln Gly Gly Ile Phe Glu Leu Lys Glu
                165                 170                 175

Asn Asp Arg Ile Phe Val Ser Val Thr Asn Glu His Leu Ile Asp Met
```

```
                180                 185                 190
Asp His Glu Ala Ser Phe Phe Gly Ala Phe Leu Val Gly
            195                 200                 205

<210> SEQ ID NO 44
<211> LENGTH: 1719
<212> TYPE: DNA
<213> ORGANISM: Propionibacterium freudenreichii

<400> SEQUENCE: 44
gtgaatccct tcgtcaagac ggcgcgcgtg gctatcacct cgacgctggt ggcaggctcg      60
ctcgccactg ccagcctcgt gtttgcacca cttgcacagg ccgattactc cccccttgcg     120
gccaccgcca cggtgaatgt gcgccagggc cccgacacct ccagctcggt gctggcgacg     180
ctctcgtcgg gtgacacggt cacccagcgg ggagccgaac aggacggctg gctgccgatc     240
acctacaacg cgccaacgc gtggatccag gcgcagtacg tggcctccac cacggccgcc      300
acccagaagg accagatctc caccgccgag ctcacggccg atgcctatgt gcgcaccgcg     360
gccaatgcga acgcctgggt gttgggcacg gcccacaccg cgacaaggt gggcatcacc      420
ggccaggcca cgcgcgacta cacgccggtg aacttctacg ccgcgccgg ttggatcgcc      480
accaagctgc tcagcgcggc cgacgcctcg gtgacatcga tcaagatcac caccgccatc     540
tcgagcgact acctgtgggt gcgtggtggc gagagcaccg cggcccagtc catcggcatg     600
ctctacccgg gtgaccgggt ggacgtgacc ggcgatcccg tcggcgggtg ggtgccgatc     660
aacttcaacg gcaagaccgc cttcgtggcc gcgaactact cgcgctatct cactgatccc     720
accgtggtca cgctgtcgac gaagaccgac gtcaccaaca aggacacggc cacctcgacg     780
ggcaccgatt cctcgacggc cggcggctcg accgccacca ccccgaccac cacggcgcca     840
accaccaccg ctcctgcaac caagccgacg accacgcccc cggccacgac gcaggccgct     900
gcgtccacga agtacacgac ggccgacgtc aacgtgcgcg tgggaccgg catcgaccag      960
cagccggtga cggtgctcaa ggagaactcg caggtggccg ccaccggcaa gacaagtggc    1020
gactggaccg aggtcagcta cgacggcgcc tcgcgctgga tcagcagcca gtacctctcg    1080
gacaccaagc aggccgaggc acccgccccg gcacctgcgc ccgatccgac gcccgccggc    1140
cccaccggaa gccggtggac cacggcggca ctgaacgcct atggcagctc cacccagccc    1200
aagccggcca ccacggtggt gcccgagggc acccaggtgg aactgaccgg caagcaggcc    1260
gatggacgct cggagtacac gtggaacggc acgacctatt ggtcggccac cgaatacctc    1320
ggcaccaatg cgccggccac gaacacctca gcgaacaccg ccaagccggg cgccaacgcg    1380
gtggagacgg cgatcaactt cgcgatgtcg aagctcggtg gccctatgt ctggggcggc     1440
accggtccgg tgggctatga ctgctccgga ctgatgcagg ccgcgtacgc ggcggccggc    1500
gtcaccctgc cgcgcgtcac ctgggaccag gtgaatgccg gcaagcaggt gtcggtcggc    1560
gacctgcagc cggcgaccct ggtgttcttc tatgacaacg ccacgtgggg catgtacatc    1620
ggcaacggca acatcgtcaa cgccctcaac gaggacgccg gcatcgtggt gaccccgatc    1680
agctatatgc cgatctcggc tgccgtccgg atcgcctga                           1719

<210> SEQ ID NO 45
<211> LENGTH: 26
<212> TYPE: PRT
<213> ORGANISM: Propionibacterium acnes

<400> SEQUENCE: 45
```

```
Met Ser Lys Val Val Ala Ser Ala Ile Ala Gly Ala Leu Ser Leu Thr
1               5                   10                  15

Ser Ala Gly Gly Leu Thr Met Val Gln Ala
            20                  25
```

<210> SEQ ID NO 46
<211> LENGTH: 30
<212> TYPE: PRT
<213> ORGANISM: Propionibacterium acnes

<400> SEQUENCE: 46

```
Met Arg Lys Ala Ile Val Thr Pro Val Ala Val Leu Ala Val Leu Val
1               5                   10                  15

Met Ala Leu Thr Gly Cys Gly Gln Lys Asn Gln Ser Gly Gly
            20                  25                  30
```

<210> SEQ ID NO 47
<211> LENGTH: 29
<212> TYPE: PRT
<213> ORGANISM: Propionibacterium acnes

<400> SEQUENCE: 47

```
Met Ala Ser Thr Pro Arg Arg Arg Trp Ala Trp Val Leu Leu Leu Val
1               5                   10                  15

Val Ala Ser Leu Val Ile Val Gly Val Tyr Arg Lys Ala
            20                  25
```

<210> SEQ ID NO 48
<211> LENGTH: 26
<212> TYPE: PRT
<213> ORGANISM: Propionibacterium acnes

<400> SEQUENCE: 48

```
Met Ser Ser Met Lys Gly Leu Ser Leu Val Leu Ala Thr Ser Phe Met
1               5                   10                  15

Leu Ser Phe Ser Pro Gly Ser Ser Phe Ala
            20                  25
```

<210> SEQ ID NO 49
<211> LENGTH: 44
<212> TYPE: PRT
<213> ORGANISM: Propionibacterium acnes

<400> SEQUENCE: 49

```
Met Glu His Arg Tyr Gly Ala Ser Gln Val Ser Gly Ser Ala Pro Arg
1               5                   10                  15

Arg Gly Arg Gly Val Ala Phe Ala Ala Ile Thr Gly Ala Ile Leu Leu
            20                  25                  30

Gly Thr Val Ala Ser Val Asp Pro Gly Ala Gln Ala
            35                  40
```

<210> SEQ ID NO 50
<211> LENGTH: 27
<212> TYPE: PRT
<213> ORGANISM: Propionibacterium acnes

<400> SEQUENCE: 50

```
Met Ser Ser Met Lys Gly Leu Ser Leu Val Leu Ala Thr Ser Phe Met
1               5                   10                  15

Leu Ser Phe Ser Pro Gly Ser Ser Phe Ala Ser
            20                  25
```

```
<210> SEQ ID NO 51
<211> LENGTH: 47
<212> TYPE: PRT
<213> ORGANISM: Propionibacterium acnes

<400> SEQUENCE: 51

Met Pro His Ser Asp Gln Pro Thr Ser Lys Arg Val Met Ser Ala Pro
1               5                   10                  15

Arg Arg Arg Met Pro Gly Trp Val Pro Val Thr Val Gly Ile Ala Val
            20                  25                  30

Val Val Ile Val Val Val Ala Val Ile Val Ser Ser Leu Arg Ser
        35                  40                  45

<210> SEQ ID NO 52
<211> LENGTH: 32
<212> TYPE: PRT
<213> ORGANISM: Propionibacterium acnes

<400> SEQUENCE: 52

Met Phe Gly Thr Pro Ser Arg Arg Thr Phe Leu Thr Ala Ser Ala Leu
1               5                   10                  15

Ser Ala Met Ala Leu Ala Ala Ser Pro Thr Val Thr Asp Ala Ile Ala
            20                  25                  30

<210> SEQ ID NO 53
<211> LENGTH: 26
<212> TYPE: PRT
<213> ORGANISM: Propionibacterium acnes

<400> SEQUENCE: 53

Met Lys Ile Asn Ala Arg Phe Ala Val Met Ala Ala Ser Val Ala Val
1               5                   10                  15

Leu Met Ala Ala Ala Pro Ile Ala Gln Ala
            20                  25

<210> SEQ ID NO 54
<211> LENGTH: 50
<212> TYPE: PRT
<213> ORGANISM: Propionibacterium acnes

<400> SEQUENCE: 54

Met Tyr Pro Val His Leu Pro Leu Arg Asn Glu Ser Glu Phe Ser Phe
1               5                   10                  15

Arg Ala His Asn His Gly Gly Thr Val Pro Ser Arg Leu Thr Arg Arg
            20                  25                  30

Ser Val Leu Ala Thr Gly Ala Val Ala Leu Pro Met Thr Ala Ala Ala
        35                  40                  45

Cys Ala
    50

<210> SEQ ID NO 55
<211> LENGTH: 27
<212> TYPE: PRT
<213> ORGANISM: Propionibacterium acnes

<400> SEQUENCE: 55

Met Arg His Met Arg Pro Leu Ile Ala Leu Ser Leu Ala Gly Leu Met
1               5                   10                  15

Thr Leu Ser Ala Cys Gly Glu Asp Val Ala Ala
            20                  25
```

<210> SEQ ID NO 56
<211> LENGTH: 31
<212> TYPE: PRT
<213> ORGANISM: Propionibacterium acnes

<400> SEQUENCE: 56

Met Asn Arg Thr Leu Lys Val Ala Ala Val Gly Ala Ile Ala Ile Leu
1               5                   10                  15

Cys Leu Ala Ala Cys Ser Asp Pro Gly Ser Asp Ser Ala Gln Ser
            20                  25                  30

<210> SEQ ID NO 57
<211> LENGTH: 24
<212> TYPE: PRT
<213> ORGANISM: Propionibacterium acnes

<400> SEQUENCE: 57

Met Glu Lys Ser Ser Phe Ala Ala Ala Asn Met Thr Ile Met Ser Glu
1               5                   10                  15

Pro Thr Thr Pro Thr Ser Gln Ala
            20

<210> SEQ ID NO 58
<211> LENGTH: 281
<212> TYPE: PRT
<213> ORGANISM: Homo sapiens

<400> SEQUENCE: 58

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr

```
                225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
                260                 265                 270

Ser Phe Phe Gly Ala Phe Leu Val Gly
                275                 280

<210> SEQ ID NO 59
<211> LENGTH: 22
<212> TYPE: PRT
<213> ORGANISM: Artificial Sequence
<220> FEATURE:
<223> OTHER INFORMATION: Signal peptide of Surface layer protein A of
      Propionibacterium freudenreichii strain CIRM BIA 118

<400> SEQUENCE: 59

Met Ala Thr Gly Ala Ala Ala Met Phe Val Thr Thr Phe Ala Gly
1               5                   10                  15

Met Ala Pro Ala Asn Ala
            20

<210> SEQ ID NO 60
<211> LENGTH: 29
<212> TYPE: PRT
<213> ORGANISM: Artificial Sequence
<220> FEATURE:
<223> OTHER INFORMATION: Signal peptide of Surface layer protein B of
      Propionibacterium freudenreichii strain CIRM BIA 118

<400> SEQUENCE: 60

Met Ser Val Arg Lys Ser Leu Thr Gly Met Ala Leu Gly Leu Ala Leu
1               5                   10                  15

Thr Ile Thr Pro Leu Ala Gly Ala Val Pro Ala Ser Ala
            20                  25

<210> SEQ ID NO 61
<211> LENGTH: 28
<212> TYPE: PRT
<213> ORGANISM: Artificial Sequence
<220> FEATURE:
<223> OTHER INFORMATION: Signal peptide of Surface layer protein D of
      Propionibacterium freudenreichii strain CIRM BIA 118

<400> SEQUENCE: 61

Met Arg Arg Phe Phe Ser Ala Ala Ile Ala Ile Leu Leu Ala Ala Thr
1               5                   10                  15

Leu Thr Pro Ala Leu Asn Ala Pro Met Ala Ser Ala
            20                  25

<210> SEQ ID NO 62
<211> LENGTH: 28
<212> TYPE: PRT
<213> ORGANISM: Artificial Sequence
<220> FEATURE:
<223> OTHER INFORMATION: Signal peptide of Surface layer protein D of
      Propionibacterium freudenreichii strain CIRM BIA 121

<400> SEQUENCE: 62

Met Arg Arg Phe Phe Ser Ala Ala Ile Ala Ile Leu Leu Ala Ala Thr
1               5                   10                  15

Leu Thr Pro Ala Leu Asn Ala Pro Met Ala Ser Ala
            20                  25
```

<210> SEQ ID NO 63
<211> LENGTH: 29
<212> TYPE: PRT
<213> ORGANISM: Artificial Sequence
<220> FEATURE:
<223> OTHER INFORMATION: Signal peptide of Surface layer protein B of
    Propionibacterium freudenreichii strain CIRM BIA 122

<400> SEQUENCE: 63

Met Ser Val Arg Lys Ser Leu Thr Gly Met Ala Leu Gly Leu Ala Leu
1               5                   10                  15

Thr Ile Thr Pro Leu Ala Gly Ala Val Pro Ala Ala Ala
            20                  25

<210> SEQ ID NO 64
<211> LENGTH: 28
<212> TYPE: PRT
<213> ORGANISM: Artificial Sequence
<220> FEATURE:
<223> OTHER INFORMATION: Signal peptide of Surface layer protein D of
    Propionibacterium freudenreichii strain CIRM BIA 122

<400> SEQUENCE: 64

Met Arg Arg Phe Phe Ser Ala Ala Ile Ala Ile Leu Leu Ala Ala Thr
1               5                   10                  15

Leu Thr Pro Ala Leu Asn Ala Pro Met Ala Ser Ala
            20                  25

<210> SEQ ID NO 65
<211> LENGTH: 33
<212> TYPE: PRT
<213> ORGANISM: Artificial Sequence
<220> FEATURE:
<223> OTHER INFORMATION: Signal peptide of Surface layer protein E of
    Propionibacterium freudenreichii strain CIRM BIA 122

<400> SEQUENCE: 65

Met Lys Thr Arg Val Arg Ser Arg Lys Pro Ala Ala Gly Leu Ala Gly
1               5                   10                  15

Ile Ala Leu Phe Ala Ser Gly Leu Ser Leu Met Ser Thr Val Ala Ser
            20                  25                  30

Arg

<210> SEQ ID NO 66
<211> LENGTH: 22
<212> TYPE: PRT
<213> ORGANISM: Artificial Sequence
<220> FEATURE:
<223> OTHER INFORMATION: Signal peptide of Surface layer protein A of
    Propionibacterium freudenreichii strain CIRM BIA 125

<400> SEQUENCE: 66

Met Ala Thr Gly Ala Ala Ala Ala Met Phe Val Thr Thr Phe Ala Gly
1               5                   10                  15

Met Ala Pro Ala Asn Ala
            20

<210> SEQ ID NO 67
<211> LENGTH: 22
<212> TYPE: PRT
<213> ORGANISM: Artificial Sequence
<220> FEATURE:
<223> OTHER INFORMATION: Signal peptide of Surface layer protein A of
    Propionibacterium freudenreichii strain CIRM BIA 129

```
<400> SEQUENCE: 67

Met Ala Thr Gly Ala Ala Ala Ala Met Phe Val Thr Thr Phe Ala Gly
1               5                   10                  15

Met Ala Pro Ala Asn Ala
            20

<210> SEQ ID NO 68
<211> LENGTH: 22
<212> TYPE: PRT
<213> ORGANISM: Artificial Sequence
<220> FEATURE:
<223> OTHER INFORMATION: Signal peptide of Surface layer protein A of
      Propionibacterium freudenreichii strain CIRM BIA 512

<400> SEQUENCE: 68

Met Ala Thr Gly Ala Ala Ala Ala Met Phe Val Thr Thr Phe Ala Gly
1               5                   10                  15

Met Ala Pro Ala Asn Ala
            20

<210> SEQ ID NO 69
<211> LENGTH: 624
<212> TYPE: DNA
<213> ORGANISM: Artificial Sequence
<220> FEATURE:
<223> OTHER INFORMATION: DNA fragment from Propionibacterium
      freudenreichii strain CIRM BIA 118 comprising the promotor and the
      signal peptide of the Surface layer protein A

<400> SEQUENCE: 69 gatccccccga ggtccacacg ccgggccgag gcgggtacac ctgccgggca ggccgggggt    60
tccggctctg ggaatggagc tgttcggtta tccaccatgt ggacgacacg caggcaccat   120
gctcgtcttc gagcggaatc acgggccccg ataactgtgt gatttgtgcg tgaaggccga   180
ttcgggggcc gttttgagcg gcgcgccgca cggataacag cgttctatgc caccgataca   240
caatagtccc caagtgcttg acaggactct tcgaagcctc tttgaagatg gctctgacta   300
ggggaaacag tgctcagtag tcaccgcgaa ggagcagtgg ctctgttact gttctagcgg   360
ctggacgggt agttcgattg atgatacgct tgcctcggca tagtgggtcg ccaatcctag   420
ggaacccatc gaaggccatg aattttccca gaggacatgg gtgttcgaac atcccggcag   480
agctcttgaa ggtcggccgt gcaccttgt ccaggcttga aaggaaacaa gttgtctgtt   540
cgtaggattg cggtggccac aggtgctgcg gccgccatgt ttgtgacgac gtttgcgggc   600
atggcgcctg cgaatgccaa ggat                                          624

<210> SEQ ID NO 70
<211> LENGTH: 30
<212> TYPE: DNA
<213> ORGANISM: Artificial Sequence
<220> FEATURE:
<223> OTHER INFORMATION: Synthetic forward primer PSlpA_fwd_BamHI

<400> SEQUENCE: 70
atgcggatcc ccccgaggtc cacacgccgg                                     30

<210> SEQ ID NO 71
<211> LENGTH: 30
<212> TYPE: DNA
<213> ORGANISM: Artificial Sequence
<220> FEATURE:
<223> OTHER INFORMATION: Synthetic reverse primer PS_SlpA-EcoRV-Rev_bis
```

```
<400> SEQUENCE: 71
atgcgatatc ggcattcgca ggcgccatgc                                30
```